(12) United States Patent
Matsubayashi et al.

(10) Patent No.: US 12,285,372 B2
(45) Date of Patent: Apr. 29, 2025

(54) CONTROL DEVICE AND BED DEVICE

(71) Applicant: PARAMOUNT BED CO., LTD., Tokyo (JP)

(72) Inventors: Toshiki Matsubayashi, Tokyo (JP); Masato Shimokawa, Tokyo (JP)

(73) Assignee: PARAMOUNT BED CO., LTD., Tokyo (JP)

( * ) Notice: Subject to any disclaimer, the term of this patent is extended or adjusted under 35 U.S.C. 154(b) by 850 days.

(21) Appl. No.: 17/272,851

(22) PCT Filed: Aug. 1, 2019

(86) PCT No.: PCT/JP2019/030307
§ 371 (c)(1),
(2) Date: Mar. 2, 2021

(87) PCT Pub. No.: WO2020/217557
PCT Pub. Date: Oct. 29, 2020

(65) Prior Publication Data
US 2021/0315755 A1    Oct. 14, 2021

(30) Foreign Application Priority Data

Apr. 22, 2019  (JP) ................. 2019-080869

(51) Int. Cl.
*A61G 7/018* (2006.01)
*A61G 7/015* (2006.01)
*G05B 19/042* (2006.01)

(52) U.S. Cl.
CPC ............. *A61G 7/018* (2013.01); *A61G 7/015* (2013.01); *G05B 19/042* (2013.01); *A61G 2203/16* (2013.01); *G05B 2219/2608* (2013.01)

(58) Field of Classification Search
CPC . A61G 7/015; A61G 7/018; G05B 2219/2608
See application file for complete search history.

(56) References Cited

U.S. PATENT DOCUMENTS

| 4,252,231 | A | * | 2/1981 | Powers | B22C 25/00 |
| | | | | | 414/928 |
| 2004/0133982 | A1 | | 7/2004 | Horitani et al. | |
| 2005/0168027 | A1 | * | 8/2005 | McMillen | B60N 2/986 |
| | | | | | 297/284.4 |
| 2007/0235995 | A1 | * | 10/2007 | Shiga | B62D 1/11 |
| | | | | | 280/775 |
| 2015/0313779 | A1 | | 11/2015 | Kume et al. | |
| 2016/0184153 | A1 | * | 6/2016 | Madsen | A61G 7/018 |
| | | | | | 340/3.31 |

(Continued)

FOREIGN PATENT DOCUMENTS

| CN | 1496730 A | 5/2004 |
| CN | 104755056 A | 7/2015 |

(Continued)

*Primary Examiner* — Mohammad Ali
*Assistant Examiner* — Vincent W Chang
(74) *Attorney, Agent, or Firm* — Birch, Stewart, Kolasch & Birch, LLP

(57) ABSTRACT

A control device includes a controller that controls, based on a first changing amount of extension/contraction of an axis of a first actuator of a bed device, a speed of the extension/contraction of the axis of the first actuator.

16 Claims, 20 Drawing Sheets

(56) References Cited

U.S. PATENT DOCUMENTS

| | | | | |
|---|---|---|---|---|
| 2016/0193095 A1* | 7/2016 | Roussy | ............... | A61G 7/0509 |
| | | | | 5/616 |
| 2016/0367419 A1* | 12/2016 | Bhai | ................. | A61G 7/05738 |
| 2020/0038270 A1* | 2/2020 | Mansfield | ............ | A61B 5/6892 |
| 2023/0235834 A1* | 7/2023 | Hielscher | ............. | F16K 31/126 |
| | | | | 251/61.2 |

FOREIGN PATENT DOCUMENTS

| | | |
|---|---|---|
| CN | 107847381 A | 3/2018 |
| JP | 2000-225166 A | 8/2000 |
| JP | 2004-141437 A | 5/2004 |
| JP | 2005-118240 A | 5/2005 |
| JP | 2008-259630 A | 10/2008 |

* cited by examiner

CONTROL DEVICE AND BED DEVICE

TECHNICAL FIELD

Embodiments of the invention relate to a control device and a bed device.

BACKGROUND ART

For example, some beds have the variable height of a bed frame. It is desired to control the bed adequately.

CITATION LIST

Patent Literature

[Patent Literature 1] JP-A-2008-259630

SUMMARY OF INVENTION

Technical Problem

Embodiments provide a control device and a bed device capable of adequately controlling the bed.

Technical Solution

According to one embodiment, a control device includes a controller. Based on a first changing amount of extension/contraction of an axis of a first actuator of a bed device, the controller controls a speed of the extension/contraction of the axis of the first actuator.

Advantages of Invention

According to the embodiments, it is possible to provide a control device and a bed device capable of adequately controlling the bed.

DESCRIPTION OF EMBODIMENTS

Figure 1A:
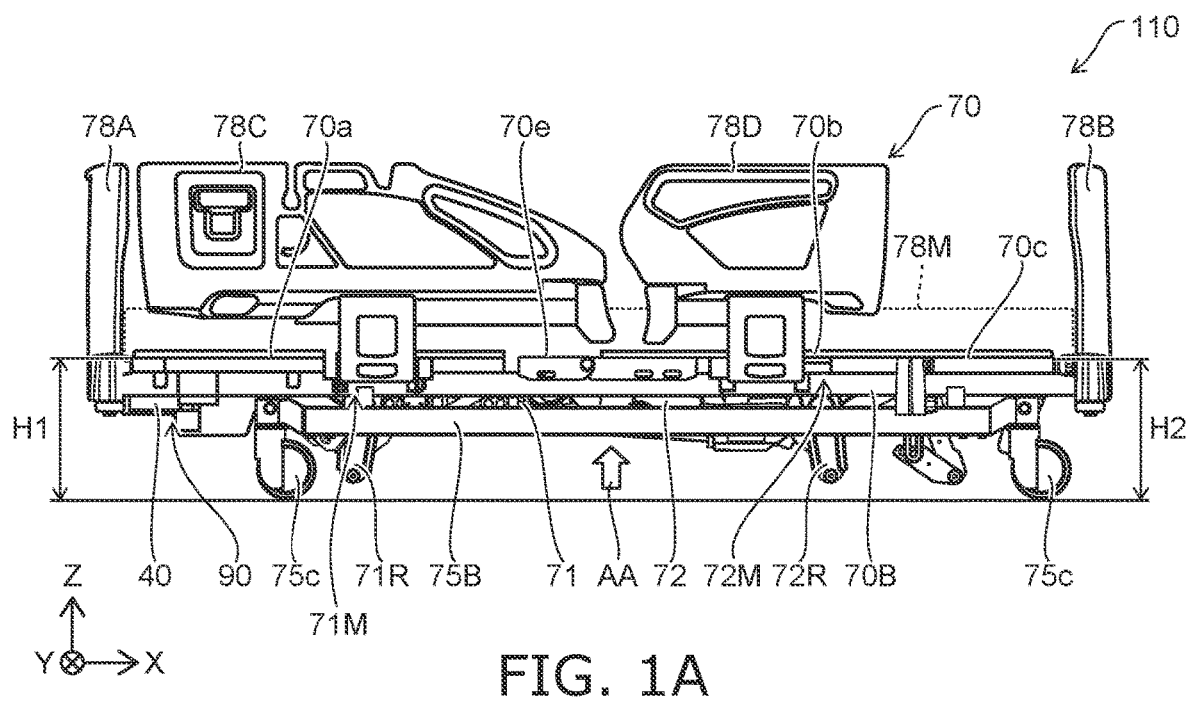
FIGS. 1A and 1B are schematic diagrams exemplifying a control device and a bed device according to a first embodiment.

Hereinafter, embodiments are described with reference to the drawings.

In the specification of the present application and the respective drawings, the similar elements having been described related to the already described drawing are assigned with the same reference numerals, and detailed explanations thereof are omitted as appropriate.

First Embodiment

Figure 1B:
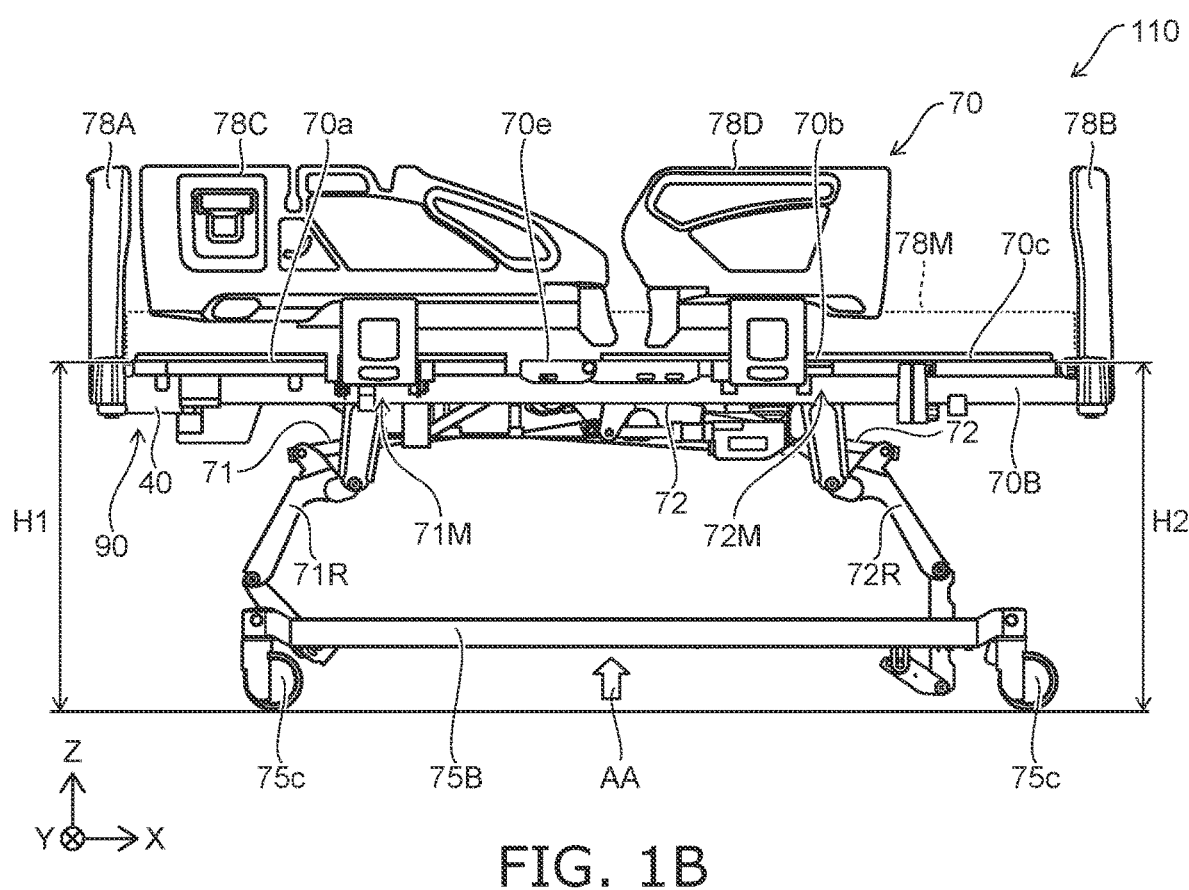
Figure 2:
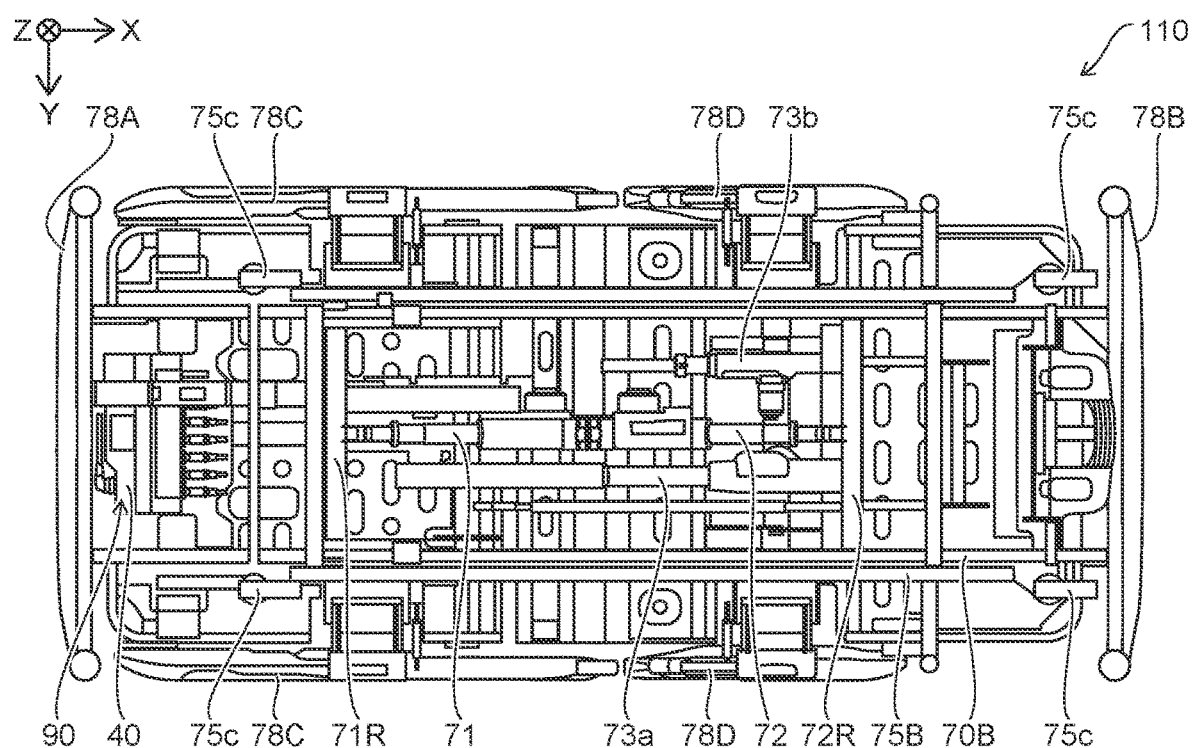
FIG. 2 is a schematic diagram exemplifying the control device and the bed device according to the first embodiment.

FIGS. 1A, 1B, and 2 are schematic diagrams exemplifying a control device and a bed device according to a first embodiment.

FIGS. 1A and 1B are side diagrams exemplifying a plurality of states of the bed device. FIG. 2 is a bottom diagram seen from an arrow AA in FIGS. 1A and 1B.

As illustrated in FIGS. 1A and 1B, a control device 90 according to the embodiment is used with a bed 70. For example, a bed device 110 includes the bed 70 and the control device 90.

For example, the control device 90 is connected to the bed 70 using an arbitrary scheme such as a wired or wireless scheme. The control device 90 may be, for example, a mobile terminal such as a smartphone.

The control device 90 includes a controller 40. In this example, the controller 40 is fixed to the bed 70.

The bed device 110 includes, for example, a base frame 75B and a bed frame 70B. For example, the bed frame 70B is located above the base frame 75B. In this example, casters 75c are provided to the base frame 75B.

For example, a back section 70a, an upper leg section 70b, a lower leg section 70c, and a seat section 70e are provided to the bed frame 70B. A mattress 78M is provided on the back section 70a, the upper leg section 70b, the lower leg section 70c, and the seat section 70e. A user of the bed 70 can lie down on the mattress 78M. In the bed 70, a headboard 78A, a foot board 78B, and the like may be provided. The side rails 78C and 78D, and the like may be provided. As will be described later, angles of the back section 70a, the upper leg section 70b, the lower leg section 70c, and the like may be variable.

In the bed 70, a direction from a head side to a foot side is set as an X-axis direction. A right-and-left direction is set as a Y-axis direction. A height direction is set as a Z-axis direction.

As illustrated in FIGS. 1A and 1B, the height of the bed 70 is variable. The height of the bed 70 is, for example, a distance in the Z-axis direction between a position of a floor surface (a lower end of the caster 75c) in the Z-axis direction and a position of a top surface of the bed frame 70B in the Z-axis direction.

In this example, the height in a portion at the head side of the bed frame 70B and the height in a portion at the foot side of the bed frame 70B are independently changeable with each other. For example, the bed frame 70B is capable of being inclined. The overall height of the bed frame 70B can be changed.

For example, one portion at the head side of the bed frame 70B is set as a first movable part 71M. One portion at the foot side of the bed frame 70B is set as a second movable part 72M.

In one example, the first movable part 71M is a head-side movable part, and the second movable part 72M is a foot-side movable part. The first movable part 71M may be a foot-side movable part, and the second movable part 72M may be a head-side movable part. Hereinafter, an example in a case where the first movable part 71M is a head-side movable part, and the second movable part 72M is a foot-side movable part will be described.

As illustrated in FIG. 2, a first actuator 71 and a second actuator 72 are provided. The first actuator 71 is capable of moving the first movable part 71M. The second actuator 72 is capable of moving the second movable part 72M.

As illustrated in FIGS. 1A and 1B, in this example, a first coupling part 71R and a second coupling part 72R are provided. The first coupling part 71R is coupled to the first movable part 71M and the first actuator 71. The first coupling part 71R generates a motion of the first movable part 71M in accordance with a motion of the first actuator 71. The second coupling part 72R is coupled to the second movable part 72M and the second actuator 72. The second coupling part 72R generates a motion of the second movable part 72M in accordance with a motion of the second actuator 72. These coupling parts serve as, for example a "link mechanism".

One portion of the first coupling part 71R is fixed to the base frame 75B. Another portion of the first coupling part 71R is fixed to the first movable part 71M of the bed frame 70B. The first actuator 71 changes a state of the first coupling part 71R. This makes a first height H1 of the first movable part 71M changeable.

One portion of the second coupling part 72R is fixed to the base frame 75B. Another portion of the second coupling part 72R is fixed to the second movable part 72M of the bed frame 70B. The second actuator 72 changes a state of the second coupling part 72R. This makes a second height H2 of the second movable part 72M changeable.

In the embodiment, the coupling part may be omitted. Alternatively, the actuator may include the coupling part. Hereinafter, an example in a case where the coupling part is provided separately from the actuator will be described.

The controller 40 of the control device 90 controls the first actuator 71. For example, the motion of the first actuator 71 changes the state of the first coupling part 71R to cause the first movable part 71M to move. This changes the first height H1. The controller 40 controls the second actuator 72. For example, the motion of the second actuator 72 changes the state of the second coupling part 72R to cause the second movable part 72M to move. This changes the second height H2.

The first actuator 71 extends and contracts, or rotates. The extension/contraction or the rotation of the first actuator 71 makes the state of the first coupling part 71R changeable. This causes the first movable part 71M to move. The second actuator 72 extends and contracts, or rotates. The extension/contraction or the rotation of the second actuator 72 makes the state of the second coupling part 72R changeable. This causes the second movable part 72M to move. Hereinafter, a case where the first actuator 71 extends and contracts, and the second actuator 72 extends and contracts will be described.

A predetermined relation between a changing amount (first changing amount) of the motion of the first actuator 71 (for example, extension/contraction) and a second changing amount of the motion of the first movable part 71M (change in the first height H1) is present. Information related to this relation is set as first relation information. This relation is based on, for example, a structure of the first actuator 71, a structure of the first coupling part 71R, a position to which the first coupling part 71R is fixed, and the like.

Similarly, a predetermined relation between a changing amount (third changing amount) of the motion of the second actuator 72 (for example, extension/contraction) and a fourth changing amount of the motion of the second movable part 72M (change in the second height H2) is present. Information related to this relation is set as second relation information. This relation is based on, for example, a structure of the second actuator 72, a structure of the second coupling part 72R, a position to which the second coupling part 72R is fixed, and the like.

For example, in a case where the speed of the extension/contraction of the first actuator 71 is constant, the speed of the change in the first height H1 is not necessarily constant.

In the embodiment, the controller 40 controls, based on the first changing amount of the extension/contraction of an axis of the first actuator 71, the speed of the extension/contraction of the axis of the first actuator 71. For example, the controller 40 controls, based on an extension/contraction amount of the first actuator 71, the speed of the extension/contraction of the first actuator 71. This can provide a control device and a bed device capable of more adequately controlling the motion of the movable part. For example, the speed of the extension/contraction of the first actuator 71 when the first actuator 71 has a first length is different from the speed of the extension/contraction of the first actuator 71 when the first actuator 71 has a second length. For example, the speed of the motion (change in the length) of the first movable part 71M in accordance with the extension/contraction of the first actuator 71 becomes substantially constant. The first actuator 71 can move the first movable part 71M. The second changing amount of the first movable part 71M having moved due to the predetermined change of the first actuator 71 is a predetermined changing amount.

For example, the controller 40 controls the first actuator, based on the first changing amount of the motion of the first actuator 71, such that the speed of the motion of the first movable part 71M during a period excluding a motion start and a motion end of the first movable part 71M becomes substantially constant. For example, the controller 40 controls the first actuator 71, based on first relation information, for example. For example, the controller 40 controls (for example, changes) the speed of the extension/contraction of the first actuator 71, based on the first relation information, such that the speed of the change in the first height H1 becomes constant. For example, the controller 40 controls (for example, changes) the speed of the extension/contraction of the first actuator 71, based on the first relation information, such that the change in the first height H1 becomes in a desired state. This can provide a control device and a bed device capable of more adequately controlling the motion of the movable part.

The controller 40 may control the second actuator 72, for example, based on second relation information. For example, the controller 40 controls (for example, changes) the speed of the extension/contraction of the second actuator 72, based on the second relation information, such that the speed of the change in the second height H2 becomes constant. For example, the controller 40 controls (for example, changes) the speed of the extension/contraction of the second actuator 72, based on the second relation information, such that the change in the second height H2 becomes in a desired state.

The controller 40 may control the first actuator 71 and the second actuator 72 based on at least either one of the first relation information and the second relation information. For example, the controller 40 may control the first actuator 71 and the second actuator 72 such that the speed of the change in the first height H1 is substantially identical with the speed of the change in the second height H2. For example, while the bed frame 70B (first movable part 71M and the second movable part 72M) maintains a desired "posture", the height of the bed frame 70B becomes changeable. For example, while a desired "posture" is maintained, it is possible to make the speed of the change in the height of the bed frame 70B substantially constant. The "posture" is, for example, "horizontal". In the "horizontal" posture, an angle of the bed frame 70B relative to an X-Y plane is, for example, ±3 degrees or less. The angle may be, for example, ±2 degrees or less. The angle may be, for example, ±1 degree or less.

Hereinafter, an example of the control device 90 (or the controller 40) will be described.

Figure 3:
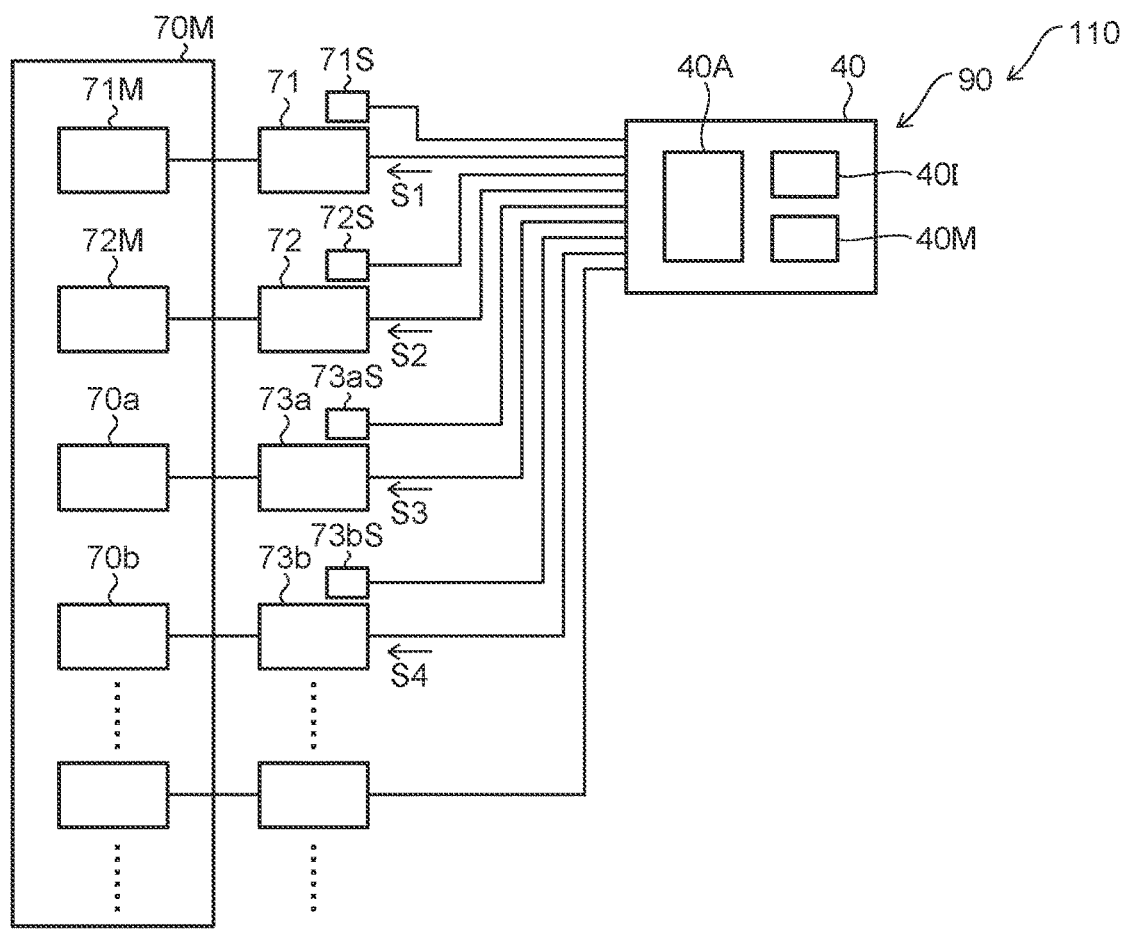
FIG. 3 is a schematic diagram exemplifying the control device and the bed device according to the first embodiment.

FIG. 3 is a schematic diagram exemplifying the control device and the bed device according to the first embodiment.

As illustrated in FIG. 3, the control device 90 (or the bed device 110) may include a memory 40M. The memory 40M stores first relation information therein. The memory 40M may further store therein second relation information. The memory 40M may be included in the controller 40. The memory 40M may be provided separately from the controller 40.

The control device 90 (or the bed device 110) may include an acquisition unit 401. The acquisition unit 401 acquires first relation information, for example, from the memory 40M. The acquisition unit 401 may further acquire second relation information, for example, from the memory 40M. The acquisition unit 401 may be included in the controller 40. The acquisition unit 401 may be provided separately from the controller 40.

The controller 40 controls the first actuator 71, for example, based on the first relation information acquired by the acquisition unit 401. The controller 40 may control the second actuator 72, for example, based on the second relation information acquired by the acquisition unit 401.

The controller 40 includes, for example, a control circuit 40A. The control circuit 40A outputs control signals (for example, first to fourth control signals S1 to S4, and the like). The control signal is, for example, an electric signal (for example, voltage).

For example, the first control signal S1 is supplied from the controller 40 to the first actuator 71. With the first control signal S1, the first actuator 71 moves, and the first movable part 71M moves. In FIG. 3, the first coupling part 71R is omitted.

For example, the second control signal S2 is supplied from the controller 40 to the second actuator 72. With the second control signal S2, the second actuator 72 moves, and the second movable part 72M moves. In FIG. 3, the second coupling part 72R is omitted.

A movable part 70M includes the first movable part 71M and the second movable part 72M. The movable part 70M may include, for example, the back section 70a and the upper leg section 70b. For example, a back actuator 73a controls an angle of the back section 70a. For example, an upper leg actuator 73b controls an angle of the upper leg section 70b.

The third control signal S3 is supplied from the controller 40 (for example, the control circuit 40A) to the back actuator 73a. With the third control signal S3, the back actuator 73a is controlled, and the angle of the back section 70a is controlled.

The fourth control signal S4 is supplied from the controller 40 (for example, the control circuit 40A) to the upper leg actuator 73b. With the fourth control signal S4, the upper leg actuator 73b is controlled, and the angle of the upper leg section 70b is controlled.

Third relation information related to a changing amount (for example, extension/contraction amount or rotation amount) of a motion of the back actuator 73a and a changing amount of a motion (angle) of the back section 70a may be provided. The controller 40 may control the back actuator 73a based on the third relation information. For example, the change in the angle of the back section 70a relative to the motion (for example, extension/contraction amount) of the back actuator 73a varies between when the angle of the back section 70a is large and small, in some cases. By controlling the back actuator 73a based on the third relation information, the angle of the back section 70a may be controlled at a desired angular speed. The desired angular speed is, for example, a substantially constant angular speed.

Fourth relation information related to a changing amount (for example, extension/contraction amount or rotation amount) of a motion of the upper leg actuator 73b and a changing amount of a motion (angle) of the upper leg section 70b may be provided. The controller 40 may control the upper leg actuator 73b based on the fourth relation information. For example, the change in the angle of the upper leg section 70b relative to the motion (for example, extension/contraction amount) of the upper leg actuator 73b varies between when the angle of the upper leg section 70b is large and small in some cases. By controlling the upper leg actuator 73b based on the fourth relation information, the angle of the upper leg section 70b may be controlled at a desired angular speed. The desired angular speed is, for example, a substantially constant angular speed.

The "first movable part" may be either one of the back section 70a and the upper leg section 70b. The "second movable part" may be the other of the back section 70a and the upper leg section 70b.

As illustrated in FIG. 3, a first detector 71S may be provided. The first detector 71S detects a state of the extension/contraction or the rotation of the first actuator 71. In a case where the first actuator 71 extends and contracts, the length in the shortest state of the first actuator 71 is set as a shortest width, and the length in the longest state of the first actuator 71 is set as a longest width. For example, the shortest width is set to 0%, and the longest width is set to 100%. The first detector 71S detects a current width (length) of the first actuator 71. The width (length) detected by the first detector 71S is x1 (0≤x1≤100). The width (length) detected by the first detector 71S corresponds to first state information. The controller 40 may control the first actuator 71 based on the first state information and the first relation information.

For example, the speed of the first movable part 71M may be calculated from the first state information (for example, position information). The controller 40 may control the first actuator 71 so as to attain a target speed. The controller 40 adjusts, for example, the voltage of the first control signal S1 so as to attain a target speed. For example, the controller 40 may change the target speed in accordance with the first state information (for example, position information).

As illustrated in FIG. 3, a second detector 72S may be provided. The second detector 72S detects a state of the extension/contraction or the rotation of the second actuator 72. The second detector 72S detects a current width (length) of the second actuator 72. The width (length) detected by the second detector 72S is x2% (0≤x2≤100). The width (length) detected by the second detector 72S corresponds to second state information. The controller 40 may control the second actuator 72 based on the second state information and the second relation information.

For example, the speed of the second movable part 72M may be calculated from the second state information (for example, position information). The controller 40 may control the second actuator 72 so as to attain a target speed. The controller 40 adjusts, for example, the voltage of the second control signal S2 so as to attain a target speed. For example, the controller 40 may change the target speed in accordance with the second state information (for example, position information).

As illustrated in FIG. 3, a back detector 73aS may be provided. The back detector 73aS detects a state of the extension/contraction or the rotation of the back actuator 73a. The width (length) detected by the back detector 73aS corresponds to third state information. The controller 40 may control the back actuator 73a based on the third state information and the third relation information.

As illustrated in FIG. 3, an upper leg detector 73bS may be provided. The upper leg detector 73bS detects a state of the extension/contraction or the rotation of the upper leg actuator 73b. The width (length) detected by the upper leg detector 73bS corresponds to fourth state information. The controller 40 may control the upper leg actuator 73b based on the fourth state information and the fourth relation information.

Hereinafter, an example of a relation between a changing amount of the motion of the actuator and a changing amount of the motion of the movable part 70M will be described.

Figure 4A:
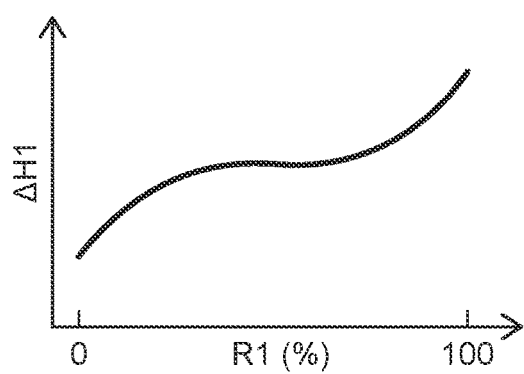
FIGS. 4A and 4B are graphs exemplifying characteristics of the bed device according to the first embodiment.
Figure 4B:
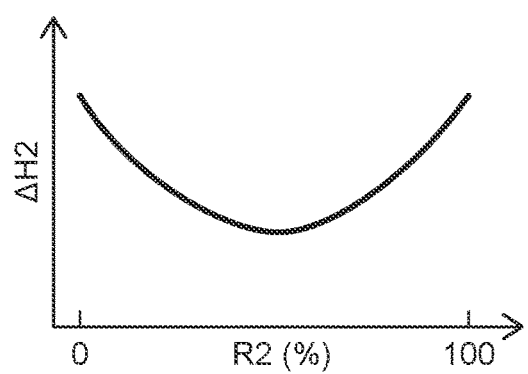

FIGS. 4A and 4B are graphs exemplifying characteristics of the bed device according to the first embodiment.

FIG. 4A corresponds to the first actuator 71 and the first movable part 71M. FIG. 4B corresponds to the second actuator 72 and the second movable part 72M.

The horizontal axis in FIG. 4A represents a state R1 (%) of the first actuator 71. In this example, the state R1 corresponds to the length (width) of the extension/contraction of the first actuator 71. When the state R1 is 0%, the first actuator 71 has the shortest length. When the state R1 is 100%, the first actuator 71 has the longest length. The longitudinal axis in FIG. 4A represents a changing amount ΔH1 of the first height H1 of the first movable part 71M. As illustrated in FIG. 4A, the changing amount ΔH1 of the first height H1 has a specific relation relative to the change in the state R1. This specific relation corresponds to the first relation information.

The horizontal axis in FIG. 4B represents a state R2 (%) of the second actuator 72. In this example, the state R2 corresponds to the length (width) of the extension/contraction of the second actuator 72. When the state R2 is 0%, the second actuator 72 has the shortest length. When the state R2 is 100%, the second actuator 72 has the longest length. The longitudinal axis in FIG. 4B represents a changing amount ΔH2 of the second height H2 of the second movable part 72M. As illustrated in FIG. 4B, the changing amount ΔH2 of the second height H2 has a specific relation relative to the change in the state R2. This specific relation corresponds to the second relation information.

The characteristic (curve) of the second relation information is not coincident with the characteristic (curve) of the first relation information in some cases.

As is understood from FIG. 4A, for example, when the state R1 is caused to change at the constant speed and the first actuator 71 is caused to extend and contract at the constant speed, the changing amount ΔH1 of the first height H1 does not change at the constant speed.

In the embodiment, the controller 40 controls the first actuator 71 based on the first relation information. For example, the controller 40 causes the state R1 (length) of the first actuator 71 to change such that the changing amount ΔH1 of the first height H1 changes at the substantially constant speed. The first height H1 of the first movable part 71M can be caused to change in a desired state (for example, at a constant speed).

As is understood from FIG. 4B, for example, when the state R2 is caused to change at the constant speed and the second actuator 72 is caused to extend and contract at the constant speed, the changing amount ΔH2 of the second height H2 does not change at the constant speed.

In the embodiment, the controller 40 controls the second actuator 72 based on the second relation information. For example, the controller 40 causes the state R2 (length) of the second actuator 72 to change such that the changing amount ΔH2 of the second height H2 changes at the substantially constant speed. The second height H2 of the second movable part 72M can be caused to change in a desired state (for example, at a constant speed).

For example, the speed of the first movable part 71M when the state R1 (for example, amount of extension) is 0% can be determined. The speed of the first movable part 71M when the state R1 (for example, amount of extension) is 100% can be determined. For example, the speed of the first movable part 71M when the state R1 (for example, amount of extension) is an arbitrary value of 1% to 99% can be determined based on the first relation information.

For example, the speed of the second movable part 72M when the state R2 (for example, amount of extension) is 0% can be determined. The speed of the second movable part 72M when the state R2 (for example, amount of extension) is 100% can be determined. For example, the speed of the second movable part 72M when the state R2 (for example, amount of extension) is an arbitrary value of 1% to 99% can be determined based on the second relation information.

Figure 5A:
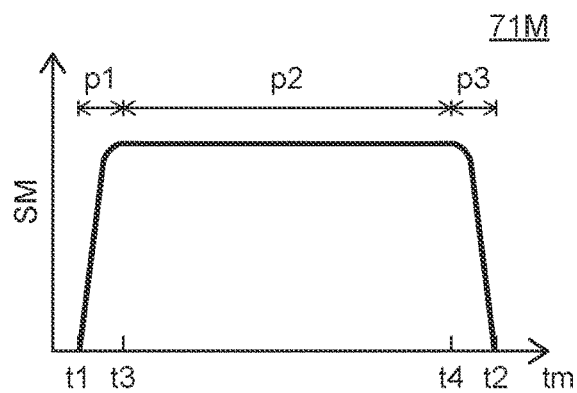
FIGS. 5A and 5B are graphs exemplifying operations of the control device and the bed device according to the first embodiment.
Figure 5B:
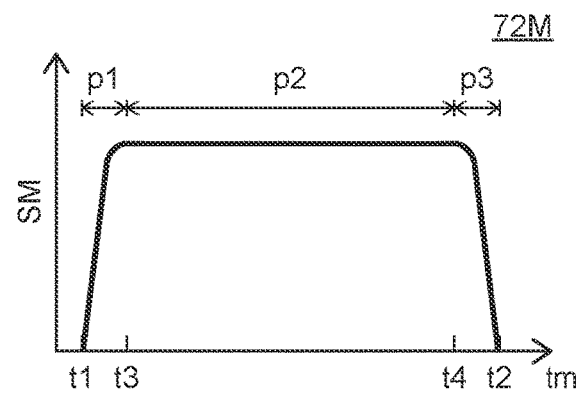

FIGS. 5A and 5B are graphs exemplifying operations of the control device and the bed device according to the first embodiment.

FIG. 5A corresponds to the first movable part 71M, and FIG. 5B corresponds to the second movable part 72M. The horizontal axis in each of these drawings represents a time tm. The longitudinal axis in FIG. 5A represents a speed SM of the change in the first height H1 of the first movable part 71M. The longitudinal axis in FIG. 5B represents the speed SM of the change in the second height H2 of the second movable part 72M. These drawings are examples of the control by the controller 40.

As illustrated in FIG. 5A, the controller 40 controls the first actuator 71, whereby the first movable part 71M starts to move at a first time t1. At a second time t2, the motion of the first movable part 71M ends. A period p1 from the first time t1 to a third time t3 after the first time t1 is a motion start period. A period p3 from a fourth time t4 to the second time t2 is a motion end period. During a period p2 from the third time t3 to the fourth time t4, for example, the first movable part 71M moves at the substantially constant speed SM.

The controller 40 controls the first movable part 71M based on the first relation information, for example, whereby, an operation exemplified in FIG. 5A can be obtained. For example, during the motion start period p1, the speed SM gradually increases. For example, during the motion end period p3, the speed SM gradually decreases. Such an operation can reduce discomfort feeling of a user.

In the embodiment, for example, the controller 40 controls the first actuator 71 such that the speed SM (first speed) of the motion of the first movable part 71M during the period (period p2) of the first movable part 71M excluding the motion start and the motion end is substantially constant.

As illustrated in FIG. 5B, for example, the second movable part 72M starts to move from the first time t1. At the second time t2, the motion of the second movable part 72M ends. During the period p2 from the third time t3 to the fourth time t4, for example, the second movable part 72M moves at the substantially constant speed SM.

In the embodiment, for example, the controller 40 controls the second actuator 72 such that the speed SM (second speed) of the motion of the second movable part 72M during the period (period p2) of the second movable part 72M excluding the motion start and the motion end is substantially constant.

In the embodiment, the controller 40 may control the first movable part 71M and the second movable part 72M with a profile different from the examples of FIGS. 5A and 5B.

The controller 40 may simultaneously control the first actuator 71 and the second actuator 72.

Figure 6:
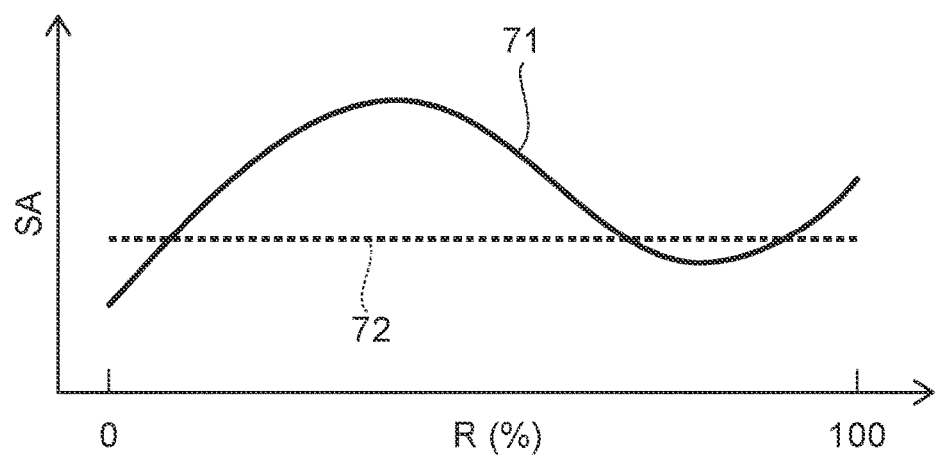
FIG. 6 is a graph exemplifying an operation of the control device and the bed device according to the first embodiment.

FIG. 6 is a graph exemplifying an operation of the control device and the bed device according to the first embodiment.

The horizontal axis in FIG. 6 represents a state R (%) of an actuator. The state R of the actuator is the state R1 of the first actuator 71 or the state R2 of the second actuator 72. The longitudinal axis in FIG. 6 represents a speed SA of the extension/contraction of the actuator. FIG. 6 illustrates a control characteristic of the first actuator 71 and a control characteristic of the second actuator 72.

In this example, the speed SA of the extension/contraction of the second actuator 72 is constant. In this case, the second height H2 of the second movable part 72M changes in accordance with the characteristic (changing amount ΔH2) illustrated in FIG. 4B.

As illustrated in FIG. 6, the speed SA of the extension/contraction of the first actuator 71 is changed in accordance with the state R (state R1). The controller 40 conducts the change (control) in the speed SA. The first control signal S1 (for example, voltage), which is supplied from the controller 40, is changed to change the speed SA of the extension/contraction of the first actuator 71.

The speed SA of the extension/contraction of the first actuator 71 is changed (controlled), for example, such that the speed SM of the change in the first height H1 that changes in accordance with the extension/contraction of the first actuator 71 is substantially coincident with the speed SM of the change in the second height H2 that changes in accordance with the extension/contraction of the second actuator 72. This can change the height of the bed frame 70B while maintaining the horizontal state, for example.

Figure 7A:
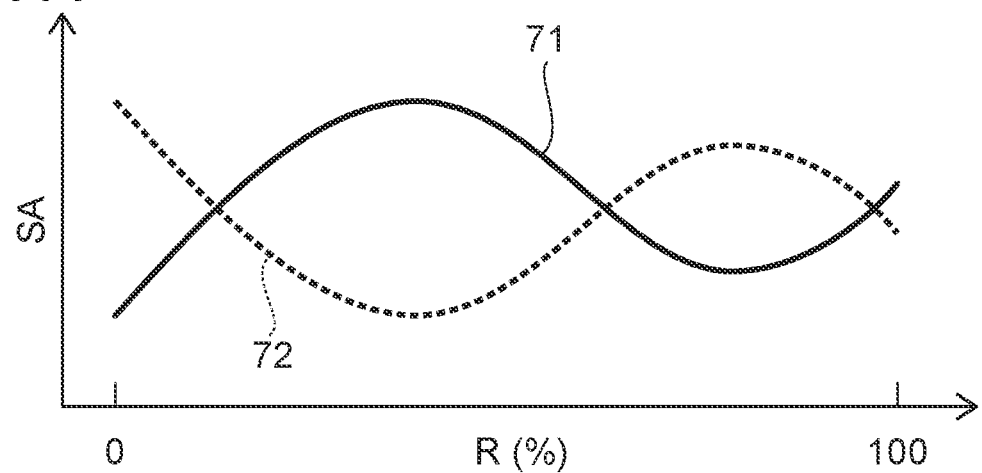
FIGS. 7A to 7C are schematic diagrams of operations of the control device and the bed device according to the first embodiment.
Figure 7B:
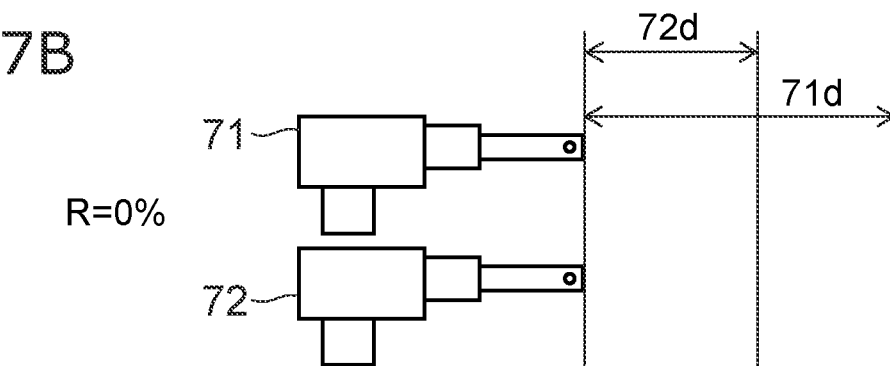
Figure 7C:
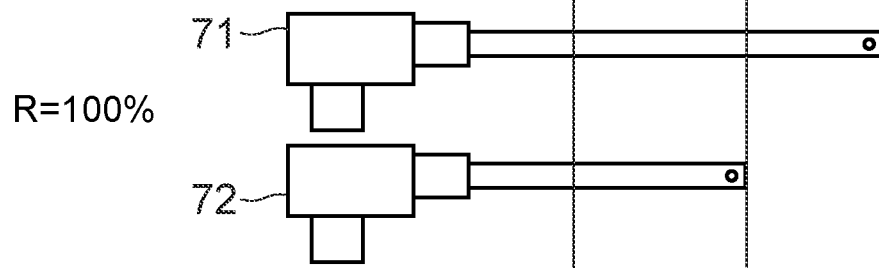

FIGS. 7A to 7C are schematic diagrams exemplifying operations of the control device and the bed device according to the first embodiment.

FIG. 7A is a graph. The horizontal axis in FIG. 7A represents the state R (%) of the actuator. The longitudinal axis in FIG. 7A represents the speed SA of the extension/contraction of the actuator. FIG. 7A illustrates a control characteristic of the first actuator 71 and a control characteristic of the second actuator 72. FIG. 7B exemplifies the actuator when the state R is 0%. FIG. 7C exemplifies the actuator when the state R is 100%. The first actuator 71 has a difference 71d as a difference in the length between when the state R is 0% and 100%. The second actuator 72 has a difference 72d as a difference in the length between when the state R is 0% and 100%. As illustrated in FIGS. 7B and 7C, in this example, the difference 71d is different from the difference 72d.

In this example, the speed SA of the extension/contraction of the first actuator 71 and the speed SA of the extension/contraction of the second actuator 72 are changed in accordance with the state R of the actuator. For example, the controller 40 changes the speed SA of the extension/contraction of the first actuator 71, based on the first relation information. For example, the controller 40 changes the speed SA of the extension/contraction of the second actuator 72, based on the second relation information. For example, the first control signal 51 (for example, voltage) and the second control signal S2 (for example voltage), which are supplied from the controller 40, are changed to change the speeds SA of the extension/contraction in the first actuator 71 and the second actuator 72.

For example, the speed SM of the change in the first height H1 of the first movable part 71M can be made to be substantially identical with, for example, the speed SM of the change in the second height H2 of the second movable part 72M. For example, while maintaining the horizontal state, the height of the bed frame 70B can be changed.

For example, the minimum height of the bed frame 70B is designed to be low. This can provide, for example, the easy-to-use bed 70. In this case, in the bed 70 in which the minimum height is designed to be low, a restriction on a lifting/lowering unit of the bed frame 70B becomes severe. This makes it difficult to lift/lower the bed frame 70B while being maintained in the horizontal state.

In the embodiment, for example, the first actuator 71 is controlled based on the first relation information, so that it is possible to lift/lower the bed frame 70B while being maintained in the horizontal state even in a case where the minimum height is low.

Second Embodiment

A second embodiment relates to a bed 19 device 310. The bed device 310 includes the abovementioned control device 90, the abovementioned first movable part 71M, and the abovementioned first actuator 71. The bed device 310 may further include the abovementioned second movable part 72M and the abovementioned second actuator 72. The bed device 310 may further include the abovementioned first coupling part 71R and the abovementioned second coupling part 72R. With the bed device 310 according to the second embodiment, it is possible to provide a bed device capable of more adequately controlling the motion of the movable part 70M.

In the first embodiment and the second embodiment, the movable part 70M may be the back section 70a. The movable part 70M may be the upper leg section 70b.

Hereinafter, an example of the bed device according to the embodiment will be described.

Figure 8:
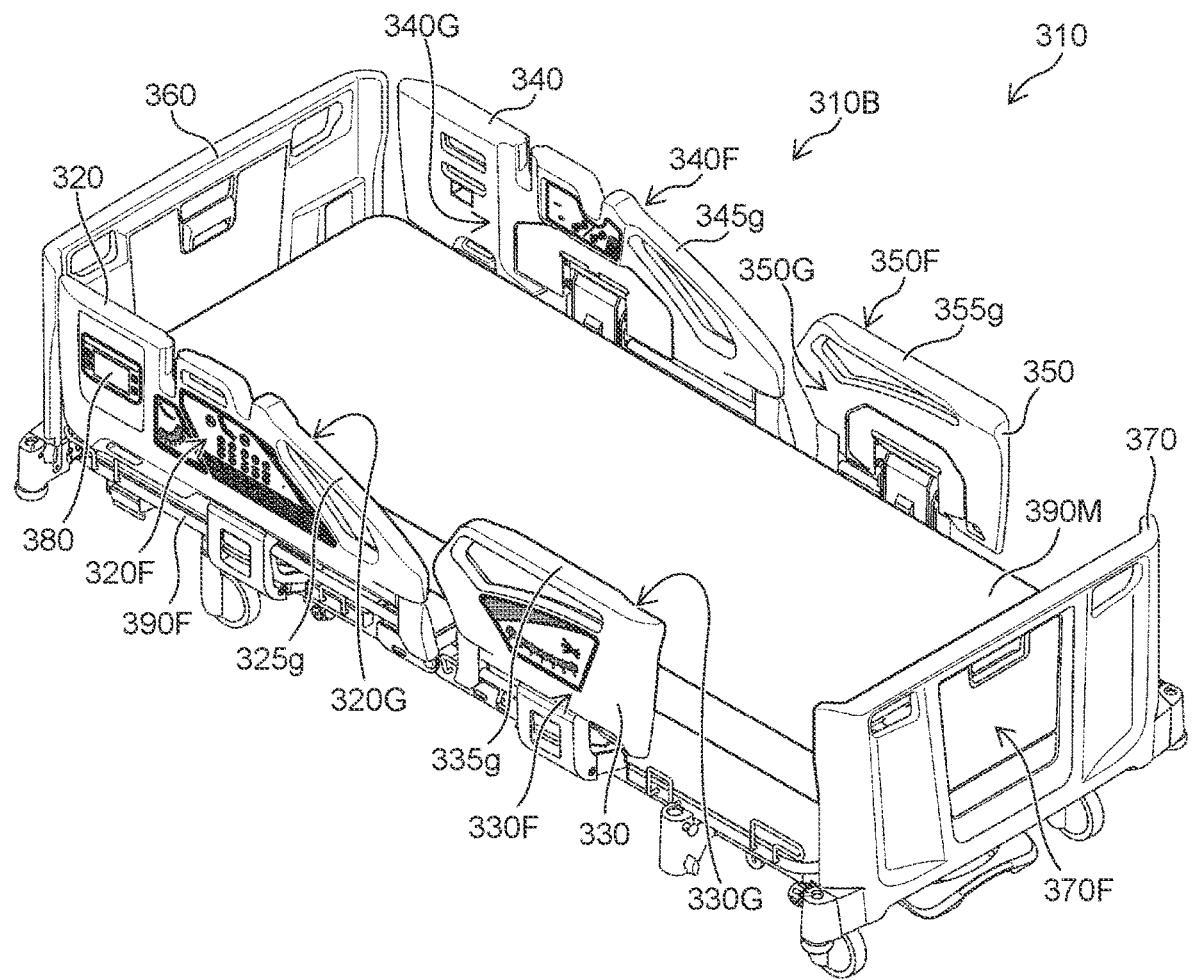
FIG. 8 is a schematic perspective view exemplifying a bed device according to an embodiment.

FIG. 8 is a schematic perspective view exemplifying the bed device according to the embodiment.

As illustrated in FIG. 8, the bed device 310 includes a head-right-side side rail 320, a leg-right-side side rail 330, a head-left-side side rail 340, a leg-left-side side rail 350, a headboard 360, and a foot board 370.

These side rails are provided, for example, to a frame 390F of a bed 310B. The sections (not illustrated in FIG. 8) are provided on the frame 390F of the bed 310B, and a mattress 390M is provided on the sections. A user of the bed 310B can lie down on the mattress 390M. The bed device 310 is used, for example, in a hospital, a care facility, or a household.

The bed device 310 is, for example, a motorized bed. The user of the bed 310B, a caretaker, or the like is capable of operating the bed device 310.

An angle (for example, angle when the horizontal plane is used as a reference) of each of the head-right-side side rail 320 and the head-left-side side rail 340 is changeable. For example, back raising, back lowering, and the like are possible. For example, an angle of the back section 70a (see FIG. 16B) is changed, so that angles of the head-right-side side rail 320 and the head-left-side side rail 340 that are attached to the back section 70a change by following the back section 70a.

The height of each of the leg-right-side side rail 330 and the leg-left-side side rail 350 is changeable. When the leg-right-side side rail 330 and the leg-left-side side rail 350 are at high positions, for example, the user can be prevented from falling off from the bed 310B. When the leg-right-side side rail 330 and the leg-left-side side rail 350 are at low positions, for example, it is easy for the user to leave the bed 310B over the leg-right-side side rail 330 and the leg-left-side side rail 350.

The head-right-side side rail 320 includes an outer surface 320F and an inner surface 320G. The leg-right-side side rail 330 includes an outer surface 330F and an inner surface 330G. The head-left-side side rail 340 includes an outer surface 340F and an inner surface 340G. The leg-left-side side rail 350 includes an outer surface 350F and an inner surface 350G.

Various kinds of switches and the like are provided to the outer surface 320F and the inner surface 320G of the head-right-side side rail 320, and the outer surface 340F and the inner surface 340G of the head-left-side side rail 340. The switches on the outer surfaces are designed, for example, so as to be convenient when being manipulated by a caretaker or a health care worker (for example, a medical doctor, a nurse, a physical therapist, or the like). Various kinds of switches and the like are also provided to the inner surfaces. The switches on the inner surfaces are designed, for example, so as to be convenient when being manipulated by the user of the bed 310B. Examples of these switches will be described later.

Handrails 325g, 335g, 345g, and 355g are respectively provided to upper-side portions of the head-right-side side rail 320, the leg-right-side side rail 330, the head-left-side side rail 340, and the leg-left-side side rail 350. Each of these handrails has a width in the up-and-down direction narrower at an inner side than at an outer side. This makes the user easy to grasp these handrails, for example.

In each of the leg-right-side side rail 330 and the leg-left-side side rail 350, the width of a top surface of each of the handrails 335g and 355g is designed to be wide. The user can sit on each of these top surfaces (sitting-on-bed-edge). This prevents the user from feeling pain in back portions of thighs in the sitting-on-bed-edge, for example.

A recessed portion is provided to each of the outer surface 320F of the head-right-side side rail 320 and the outer surface 340F of the head-left-side side rail 340. The bed manipulation device 380 is attachable to this recessed portion. The bed manipulation device 380 is also attachable to an outer surface 370F of the foot board 370. The bed manipulation device 380 will be described later.

Hereinafter, examples of the side rails will be described.

Figure 9A:
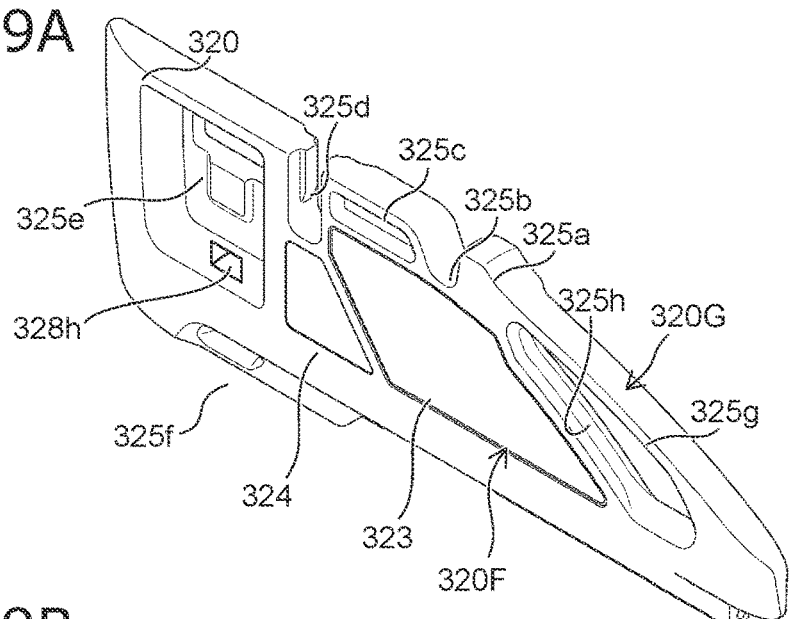
FIGS. 9A to 9C are schematic diagrams partially exemplifying the bed device according to the embodiment.
Figure 9B:
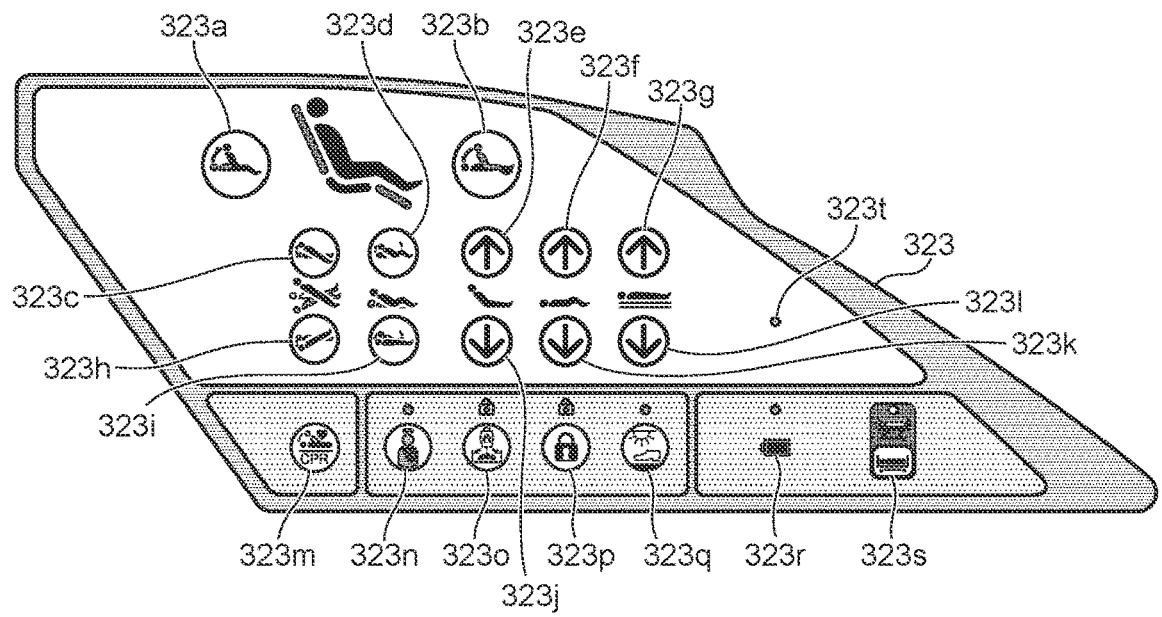
Figure 9C:
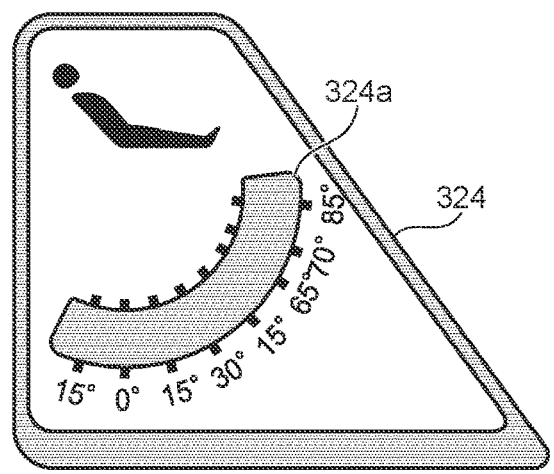

FIGS. 9A to 9C are schematic diagrams partially exemplifying the bed device according to the embodiment.

As illustrated in FIG. 9A, a through-hole 325h is provided to an upper-side portion of the head-right-side side rail 320. The through-hole 325h forms the handrail 325g.

A protruding portion 325a, a recessed portion 325b, a head-side protruding portion 325c, and a head-side recessed portion 325d are further provided to the upper-side portion of the head-right-side side rail 320. The protruding portion 325a can be used as a support part that supports a body of the user, for example. When the head-right-side side rail 320 is raised (back raising state), the recessed portion 325b can be used as the support part that supports the body of the user, for example.

It is easy for the user to grasp the head-side protruding portion 325c. For example, at the time of the back raising or the back lowering, the head-side protruding portion 325c can support the body of the user easily. The head-side protruding portion 325c is provided with a through-hole. This allows the head-side protruding portion 325c to be used as a handrail.

Various kinds of medical lines can be put into the head-side recessed portion 325d. The various kinds of lines are easy to be stable. The various kinds of medical lines include, for example, cables or tubes of a respirator, various kinds of medical engineering (ME) devices, and the like. By passing the various kinds of lines through the head-side recessed portion 325d, for example, these lines can be prevented from being tangled.

A switch unit 323, an angle meter 324, a through-hole 325e (for example, hook portion), and a lower through-hole 325f (for example, urine bag hook) are provided to the outer surface 320F of the head-right-side side rail 320. The bed manipulation device 380 can be hung in the through-hole 325e. The urine bag can be hung in the lower through-hole 325f. A trash box or the like can be hung in the lower through-hole 325f. For example, a hole 328h is provided below the through-hole 325e. A cable of the bed manipulation device 380 can be passed through the hole 328h. The cable is electrically connected to a connector provided to the bed device 310 via the hole 328h. The cable can be prevented from touching a floor. The cable can be made to be short.

FIG. 9B exemplifies the switch unit 323.

The switch unit 323 is, for example, a membrane switch (for example, health care worker membrane switch). The switch unit 323 includes switches 323a to 323q.

When the switch 323a is pressed, "cardiac raising" is conducted. When the switch 323b is pressed, "cardiac lowering" is conducted. The "cardiac raising" causes the bed 310B to be at a cardiac position (see FIG. 16B). The "cardiac raising", the bed 310B operates toward the cardiac position in a state where an angel between the back section 70a and the upper leg section 70b does not become extremely small, while maintaining a state where the upper leg section 70b is raised from the horizontal angle. In the state where the angel between the back section 70a and the upper leg section 70b does not become extremely small, the angle is less than 90 degrees. In the state where the angel between the back section 70a and the upper leg section 70b does not become extremely small, a comfortable posture is held while preventing an excess abdominal pressure from being applied to the user. For example, when the user is inclined without raising the upper legs, the user slides down in some cases. The state where the upper leg section 70b is raised from the horizontal angle prevents the user from sliding down. By the "cardiac lowering", the bed 310B operates toward a state where a back angle is 0 degree, an upper leg angle is 0 degree, and an inclined angle is 0 degree, in a state where an angle between the back section 70a and the upper leg section 70b does not become extremely small, while maintaining a state where the upper leg section 70b is raised from the horizontal angle.

When the switch 323c is pressed, "reverse expansion" is conducted. When the switch 323h is pressed, "expansion" is conducted. In the "expansion", a head is lowered. In the "reverse expansion", legs are lowered.

When the switch 323d is pressed, "KIND raising" is conducted. In the "KIND raising", angles of the back section 70a and the upper leg section 70b change in a ganged manner. When the switch 323i is pressed, "KIND lowering" is conducted. In the "KIND lowering", angles of these sections change in a ganged manner. For example, when angles of the back section 70a and the upper leg section 70b become large in a ganged manner, the angle of the upper leg section 70b becomes large firstly, and the angle of the other section becomes large thereafter. This can prevent the patient (user) from deviating. In the "KIND raising", a state where the angle of the back section 70a is 70 degrees corresponds to an operation completion angle. The angle of the upper leg section 70b is an angle having followed the angle of the back section 70a.

In the "KIND raising", firstly, the back angle is 0 degree, and the upper leg angle is 0 degree. Next, the back angle becomes 5 degrees, and the upper leg angle becomes 0 degree. Next, the back angle becomes 15 degrees, and the upper leg angle becomes 10 degree. In addition, the back angle becomes 30 degrees, the upper leg angle becomes 25 degrees, the back angle becomes 50 degrees, and the upper leg angle becomes 25 degrees. Thereafter, the back angle becomes 70 degrees, and the upper leg angle becomes 0 degree. In the "KIND raising", the back angle and the upper leg angle become large in a ganged manner halfway. When the back angle becomes a certain angel or more, the upper leg angle reduced toward 0 degree.

In the "KIND lowering", firstly, the back angle is 70 degrees, and the upper leg angle is 0 degree. Next, the back angle becomes 50 degrees, and the upper leg angle becomes 25 degrees. In addition, the back angle becomes 30 degrees, and the upper leg angle becomes 25 degrees. In addition, the back angle becomes 15 degrees, and the upper leg angle becomes 20 degrees. In addition, the back angle becomes 0 degree, and the upper leg angle becomes 5 degrees. Thereafter, the back angle becomes 0 degree, and the upper leg angle becomes 0 degree.

When the switch 323e is pressed, "back raising" is conducted. When the switch 323j is pressed, "back lowering" is conducted.

When the switch 323f is pressed, "upper leg raising" is conducted. When the switch 323k is pressed, "upper leg lowering" is conducted.

When the switch 323g is pressed, "height raising" is conducted. When the switch 323l is pressed, "height lowering" is conducted. When the height is raised in the inclined state of the bed 310B, the height rises while maintaining the inclined angle. The same applies to the "lowering". The bed 310B stops once when reaching the highest floor height while maintaining the inclined state. After the bed 310B has stopped, when the height raising button (switch 323g) is again pressed, a high priority is given to raise the height of the bed 310B, and the height rises while making the inclined angle be 0 degree. The same applies to the "lowering".

The switches 323c to 323g for the "raising" are located above the switches 323h to 323l for the "lowering". For example, there is a possibility that the user of the bed 310B may unintentionally touch a switch of the switch unit 323. The user of the bed 310B is more likely to touch the upper-side portion than the lower-side portion. The switches 323c to 323g for the "raising" are located at the upper side, so that even in a case where the user has erroneously touched the upper-side portion, a risk can be suppressed more effectively than a case where the user has touched the switches 323h to 323l.

When the switch 323m is pressed, "CPR lowering" is conducted. In the "CPR lowering", a bed state suitable for cardio pulmonary resuscitation (CPR) is obtained. In a state of the "CPR lowering", the upper leg section 70b and the lower leg section 70c become flat. In the "CPR lowering", the floor height of the bed 310B is set to be low. In a case of the inclined state, the inclined angle also becomes 0 degree. For example, an operation order is as follows. The back angle is set to 0 degree (while the back section 70a is caused to move, the upper leg section is also caused to approach 0 degree). Next, the inclined angle is set to 0 degree. Next, the height is lowered. Next, the upper leg angle is set to 0 degree. For example, the bed 310B may become in a state of the minimum floor height. For example, in the bed 310B, with the operation of "height lowering", a position (temporal stop height) at which the bed temporarily stops may be provided. In a state before the "CPR lowering", when the height is higher than this temporal stop height, the "CPR lowering" causes the height of the bed 310B to be the temporal stop height. At the temporal stop height, a distance from the floor to the section top surface is approximately 42 cm.

For example, in one example, when the switch 323m is subjected to "long pressing", "CPR lowering" is conducted. The time of the "long pressing" is, for example, 2 seconds or longer. In another example, when the switch 323m is subjected to "double pressing", "CPR lowering" is conducted. In a case where the switch 323m is subjected to the "double pressing", the time between the "first pressing" and the "second pressing" is within 5 seconds.

The operations other than the CPR operation start when the button is pressed. The CPR operation is quickly operated during an emergency, so that a person who operates the button (switch 323m) for the CPR operation hesitates to press the button for the CPR operation in some cases. As described above, for example, the switch 323m is subjected to the "long pressing" or the "double pressing", whereby the CPR operation is conducted. This allows the CPR operation to be conducted with less hesitation.

The "CPR lowering" is a motorized CPR operation. In addition to this, a manual CPR operation may be conducted.

The switch 323n is a "nurse call". When the switch 323n is pressed, nurse call outgoing is conducted. Information is transmitted to a nurse call system.

When the switch 323o is pressed, the manipulation of switches (which are described later) that are provided to the inner surface 320G of the head-right-side side rail 320 becomes in a "prohibition state". When the switch 323p is pressed, the entire manipulation related to the motion (actuator) of the bed 310B becomes in the "prohibition state". In this case, the "nurse call", the foot lamps, and the like are capable of operating.

When the switch 323q is pressed, the foot lamps that are provided to the bed 310B and the like are turned on.

In this example, the switch unit 323 includes displays 323r to 323t. The display 323r displays the remaining quantity of the battery. The display 323s is turned on (for example, orange) when the floor height is not the minimum. The display 323s is turned off when the floor height is the minimum.

The display 323t conducts error display. At the normal time, the display 323t is turned off. In the "U-system abnormality", lighting-up for 1 second and lighting-out for 1 second are repeated. In the "H-system abnormality", lighting-up for 0.2 seconds and lighting-out for 0.2 seconds are repeated.

A higher priority is given to the manipulation with the switch unit 323 (for example, health care worker membrane switches) of the outer surface 320F than the manipulation with a switch unit (for example, user membrane switches), which is described later, that is provided to the inner surface 320G. For example, when switches at the outer side and the inner side are simultaneously pressed, neither of the switches operates. For example, while the back raising is conducted with the switch at the outer side, when the upper leg raising button is pressed at the inner side, the operation of the bed 310B stops. When both of the buttons are released and pressed again, the bed 310B operates.

FIG. 9C exemplifies an angel meter 324 that is provided to the outer surface 320F of the head-right-side side rail 320.

A recessed portion is provided to the head-right-side side rail 320, and a spherical body (for example, metal ball), which is provided to the recessed portion, constitutes the angle meter 324. When the back section is raised, the spherical body rolls in the recessed portion. The angle display in a display 324a of the angle meter 324 changes in accordance with the position of the spherical body. The user can know an overview of the back angle by the angle meter 324.

Figure 10A:
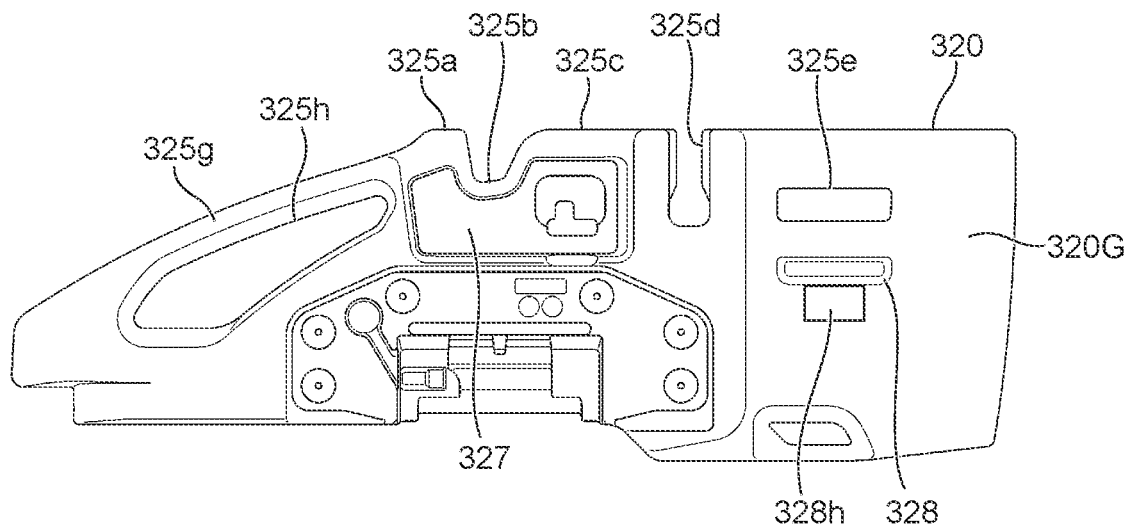
FIGS. 10A and 10B are schematic diagrams partially exemplifying the bed device according to the embodiment.
Figure 10B:
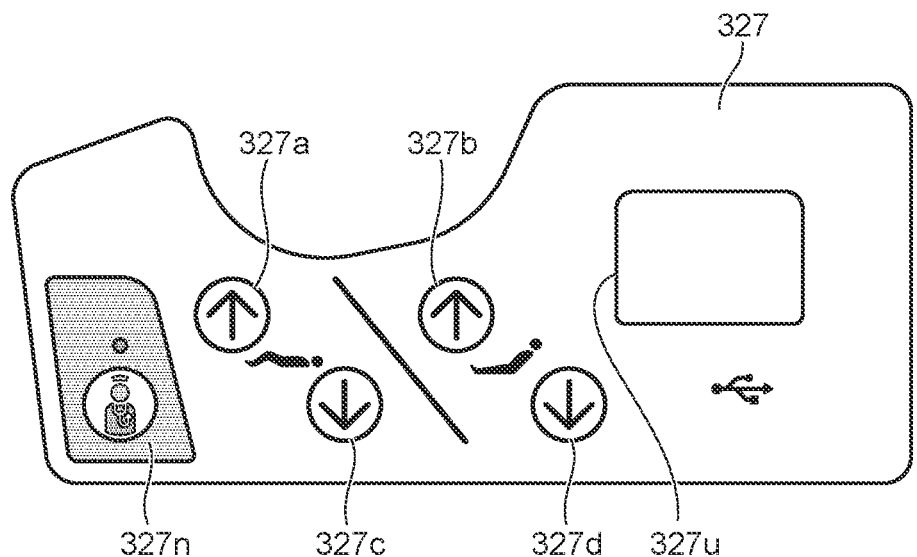

FIGS. 10A and 10B are schematic diagrams partially exemplifying the bed device according to the embodiment.

As illustrated in FIG. 10A, a recessed portion 328 is provided to the inner surface 320G of the head-right-side side rail 320. The recessed portion 328 can be used as a hook. The hole 328h is provided below the recessed portion 328. In addition, a switch unit 327 is provided to the inner surface 320G. The switch unit 327 is, for example, a membrane switch (for example, a user membrane switch or a patient membrane switch).

As illustrated in FIG. 10B, the switch unit 327 includes switches 327a to 327d. The switch unit 327 may include a switch 327n.

When the switch 327a is pressed, "leg raising" is conducted. When the switch 327c is pressed, "leg lowering" is conducted.

When the switch 327b is pressed, "back raising" is conducted. When the switch 327d is pressed, "back lowering" is conducted.

The switch 327n provided to the inner surface 320G. The switch 327n is a "nurse call".

A USB terminal 327u is provided to the inner surface 320G. A USB plug can be inserted into the USB terminal 327u to allow electric charging and the like to be conducted.

The configuration of the head-right-side side rail 320 as the above is applied to that of the head-left-side side rail 340.

Figure 11A:
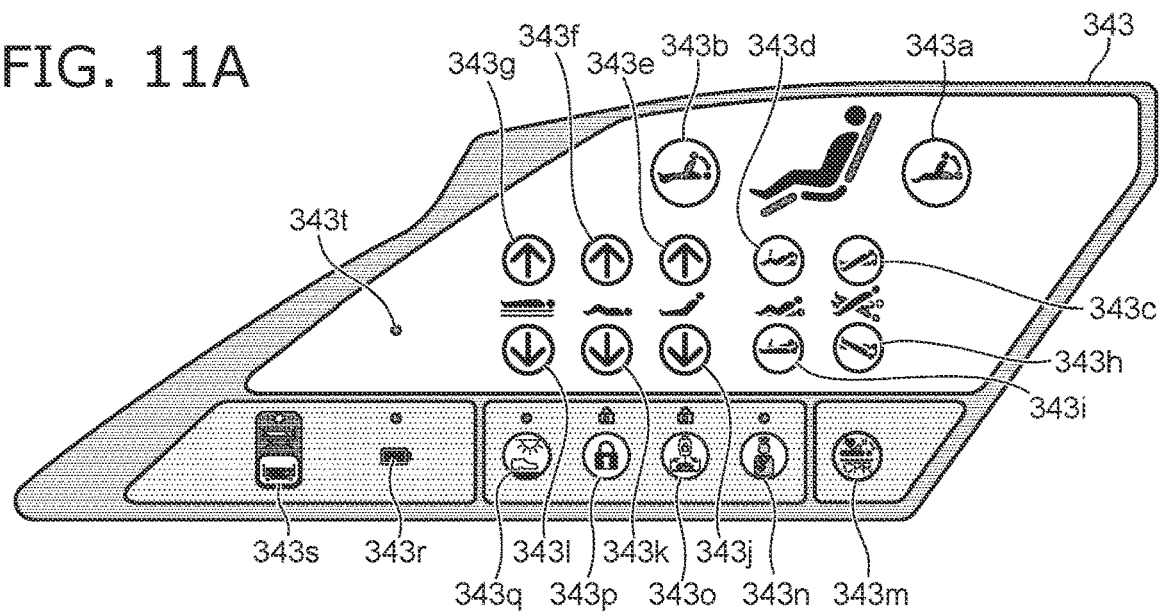
FIGS. 11A to 11C are schematic diagrams partially exemplifying the bed device according to the embodiment.
Figure 11B:
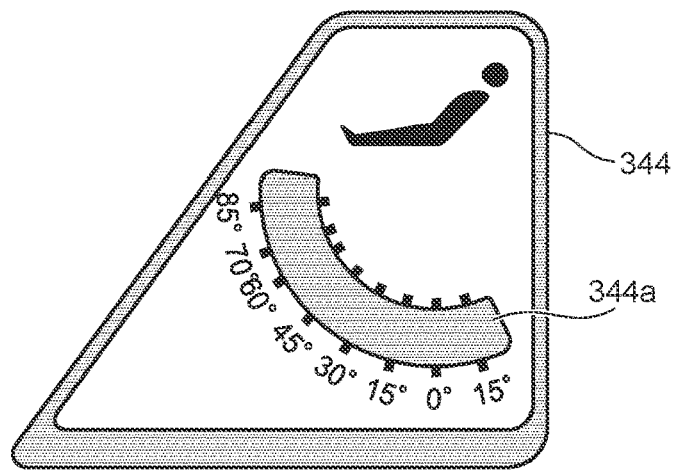
Figure 11C:
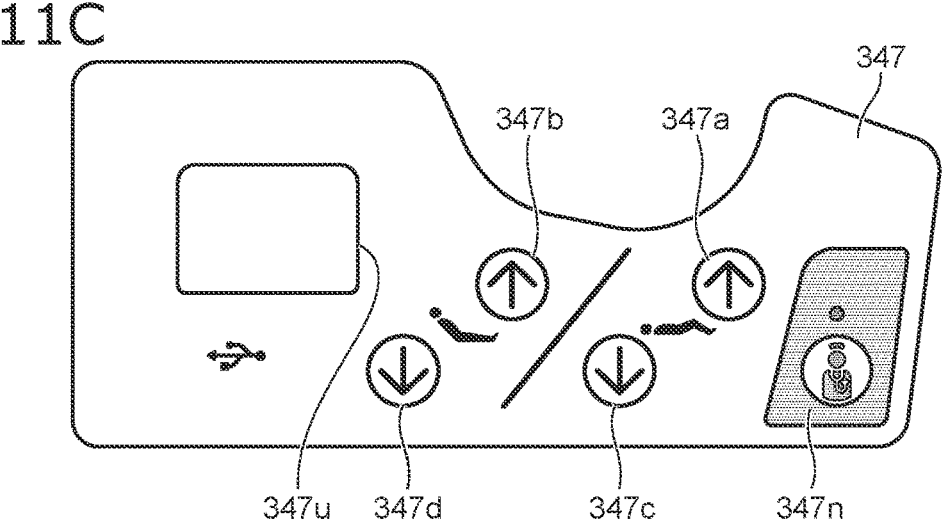

FIGS. 11A to 11C are schematic diagrams partially exemplifying the bed device according to the embodiment.

FIGS. 11A and 11B exemplify a switch unit 343 and an angle meter 344 that are provided to the outer surface 340F of the head-left-side side rail 340. As illustrated in FIG. 11A, the switch unit 343 includes switches 343a to 343q. The switches 343a to 343q have functions similar to those of the switches 323a to 323q. In this example, the switch unit 343 includes displays 343r to 343t. The displays 343r to 343t have functions similar to those of the displays 323r to 323t.

FIG. 11B exemplifies the angle meter 344. The angle meter 344 has a structure and a function similar to those of the angle meter 324. The user can know an overview of the back angle by a display 344a of the angle meter 344.

As illustrated in FIG. 11C, a switch unit 347 is provided to the inner surface 340G of the head-left-side side rail 340 (see FIG. 8). The switch unit 347 has a structure and a function similar to those of the switch unit 327. The switch unit 347 includes switches 347a to 347d. The switches 347a to 347d have functions similar to those of the switches 327a to 327d. A switch 347n and a USB terminal 347u are provided to the inner surface 320G. The USB terminal 347u may be omitted.

Figure 12A:
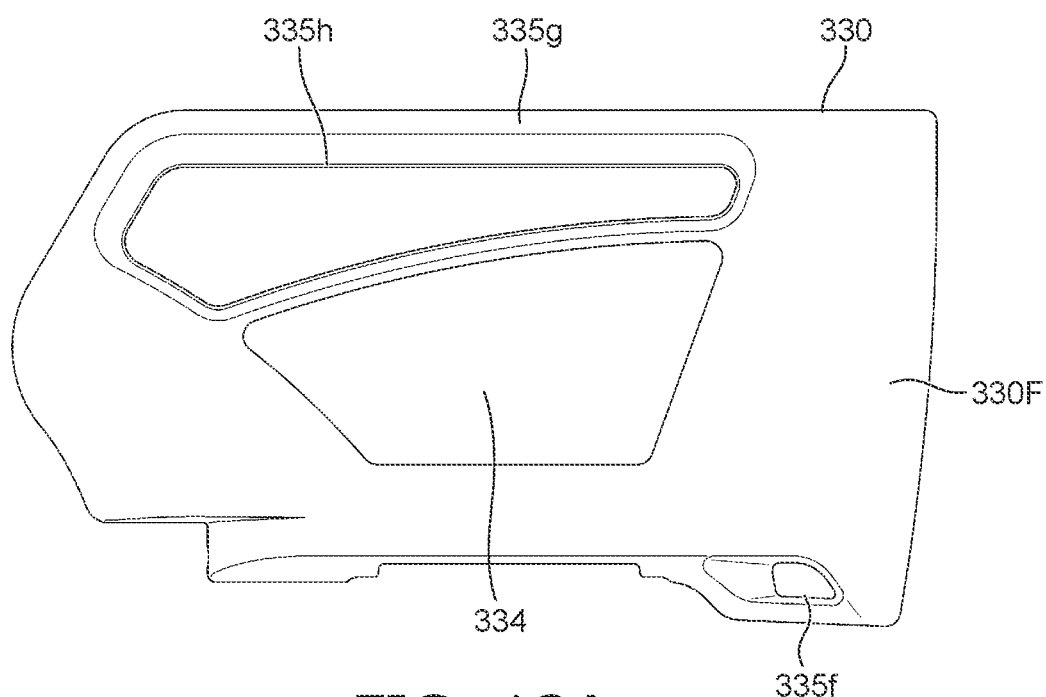
FIGS. 12A and 12B are schematic diagrams partially exemplifying the bed device according to the embodiment.
Figure 12B:
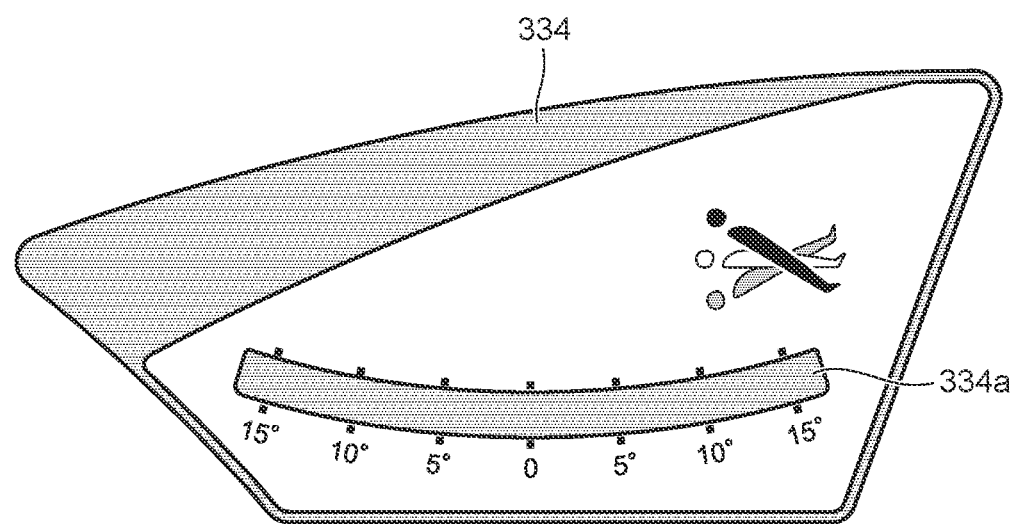

FIGS. 12A and 12B are schematic diagrams partially exemplifying the bed device according to the embodiment.

As illustrated in FIG. 12A, the handrail 335g is provided to the leg-right-side side rail 330. The handrail 335g is formed by a through-hole 335h. A lower through-hole 335f (for example, urine bag hook) is provided to a lower portion of the leg-right-side side rail 330. The urine bag or the like can be hung in the lower through-hole 335f.

An angle meter 334 is provided to the outer surface 330F of the leg-right-side side rail 330 (see FIG. 12B). The angle meter 334 has a structure similar to that of the angle meter 324. The user can know an overview of the angle by a display 334a of the angle meter 334.

Figure 13:
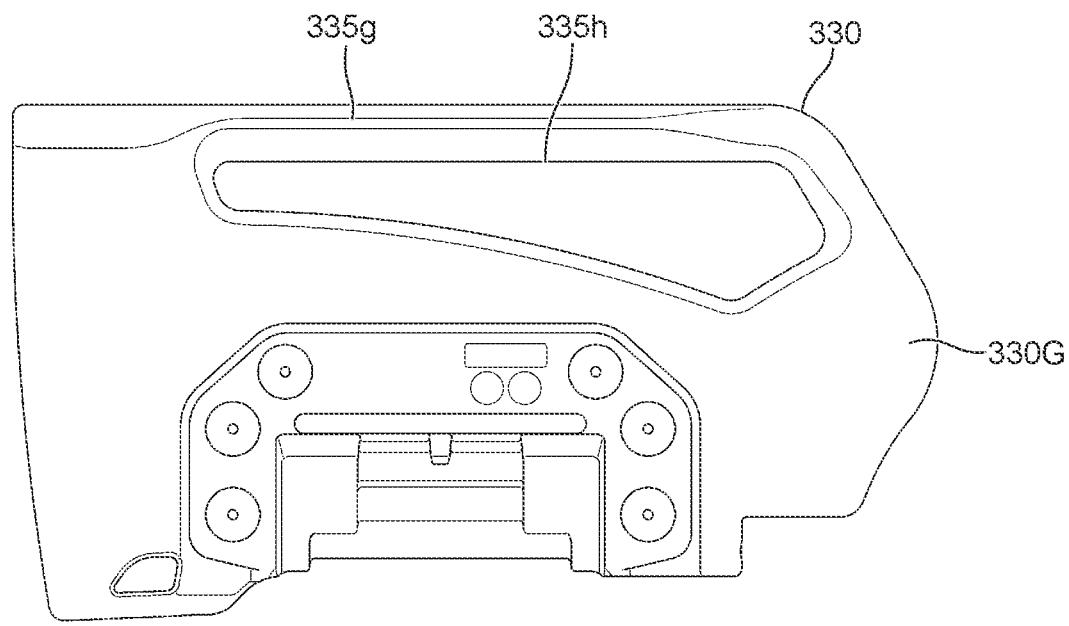
FIG. 13 is a schematic diagram partially exemplifying the bed device according to the embodiment.

FIG. 13 is a schematic diagram partially exemplifying the bed device according to the embodiment.

As illustrated in FIG. 13, the handrail 335g can be obtained from the through-hole 335h formed in the leg-right-side side rail 330.

Figure 14:
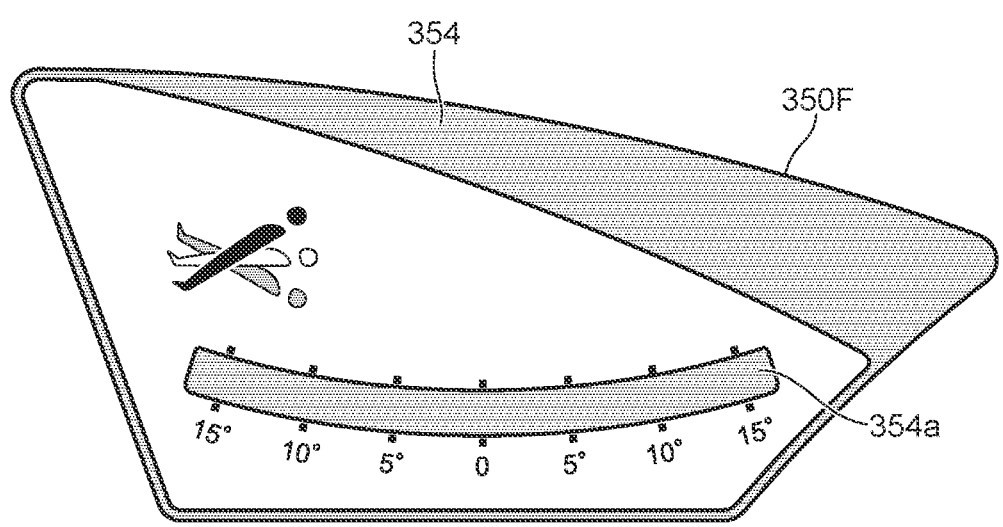
FIG. 14 is a schematic diagram partially exemplifying the bed device according to the embodiment.

FIG. 14 is a schematic diagram partially exemplifying the bed device according to the embodiment.

FIG. 14 exemplifies an angle meter 354 provided to the outer surface 350F of the leg-left-side side rail 350. The angle meter 354 has a structure similar to that of the angle meter 324. The user can know an overview of the angle by a display 354a of the angle meter 354.

Figure 15A:
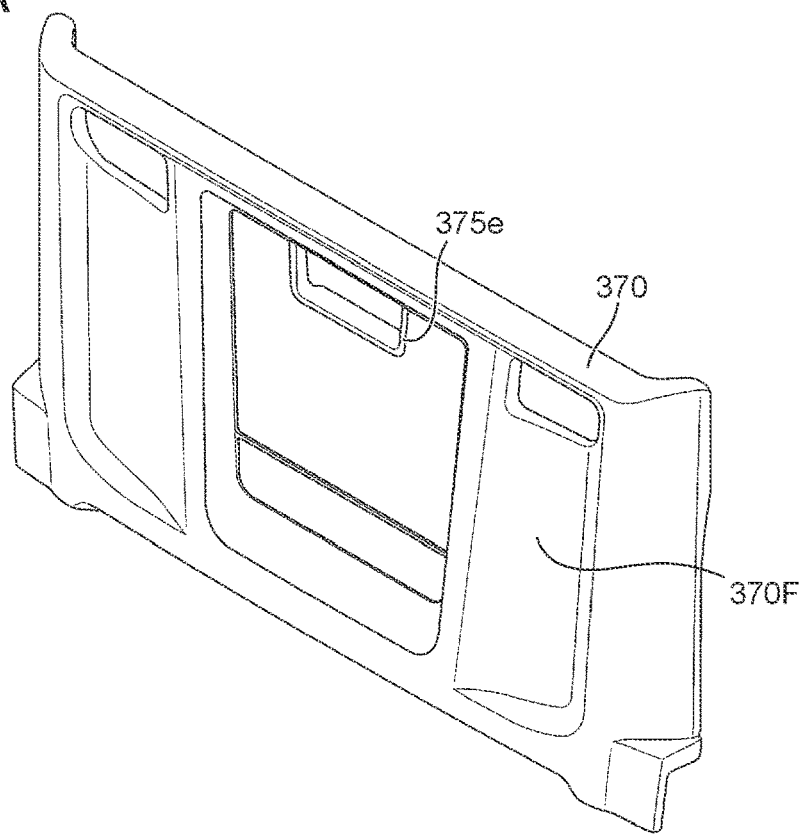
FIGS. 15A and 15B are schematic diagrams partially exemplifying the bed device according to the embodiment.
Figure 15B:
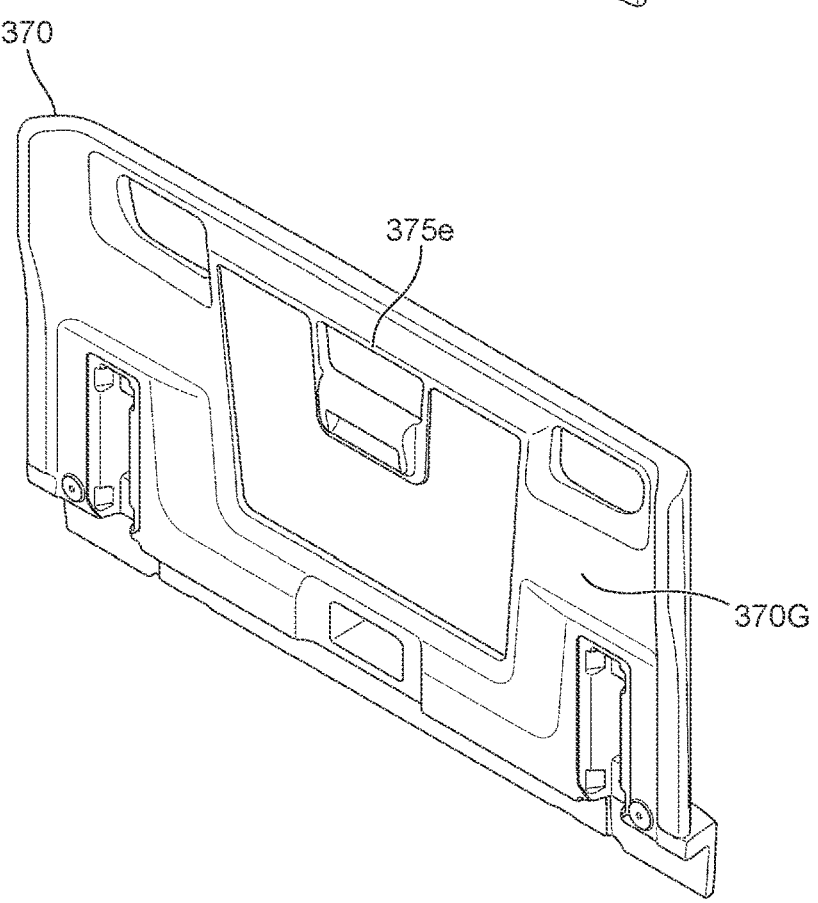

FIGS. 15A and 15B are schematic diagrams partially exemplifying the bed device according to the embodiment.

As illustrated in FIG. 15A, a through-hole 375e (for example, hook portion) is provided to the outer surface 370F of the foot board 370. The bed manipulation device 380 can be hung in the through-hole 375e. As illustrated in FIG. 15B, the through-hole 375e penetrates through an inner surface 370G of the foot board 370.

In the bed manipulation device 380, display of various kinds of settings related to the bed 310B and the body weight of the user is possible. As a "physical button" in the bed manipulation device 380, a "home button" is provided. An example of the bed manipulation device 380 will be described later.

Figure 16A:
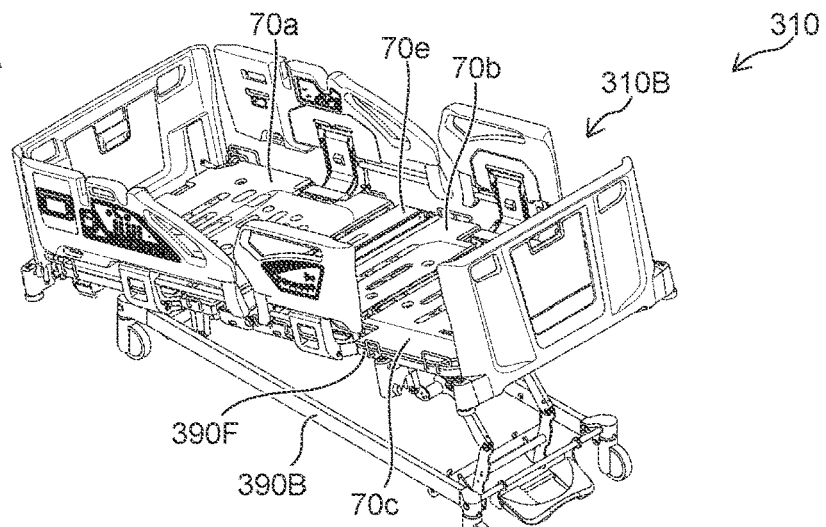
FIGS. 16A to 16C are schematic perspective views exemplifying operations by the bed device according to the embodiment.
Figure 16B:
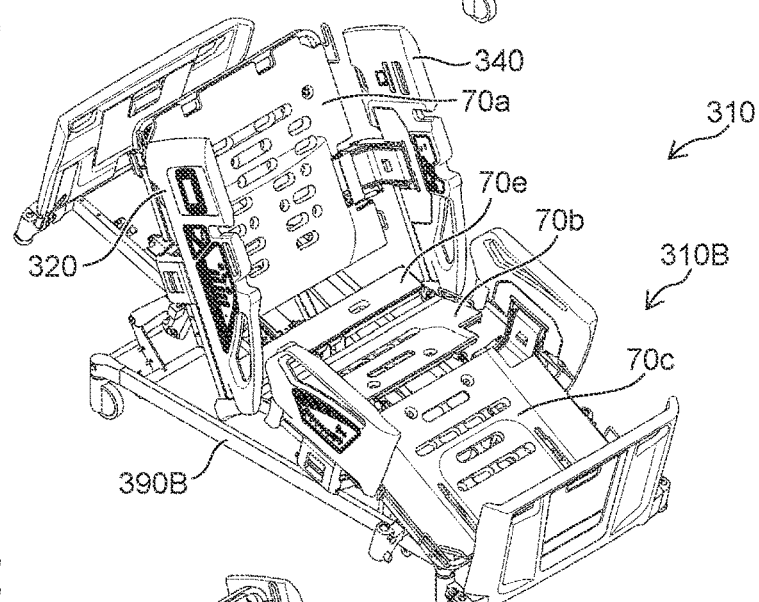
Figure 16C:
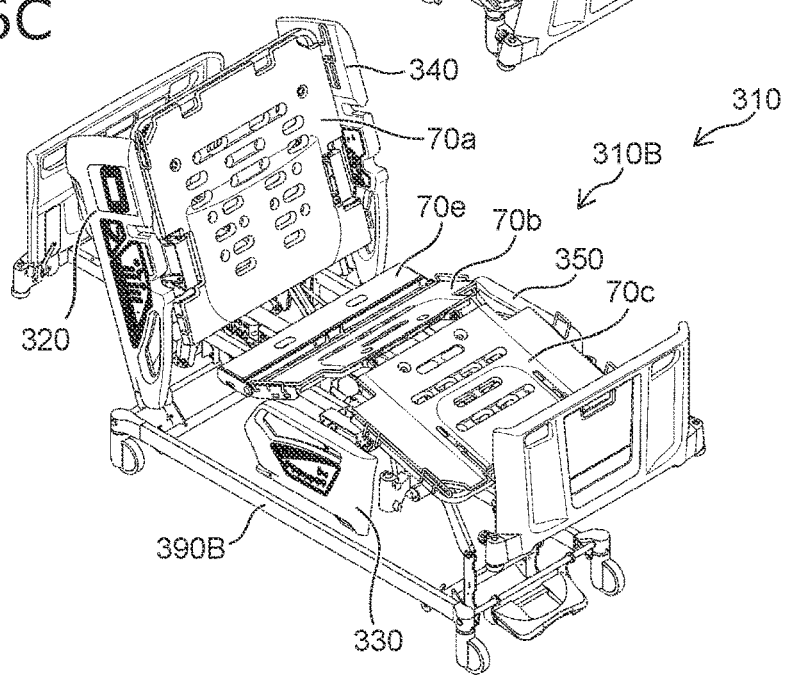

FIGS. 16A to 16C are schematic perspective views exemplifying operations of the bed device according to the embodiment.

These drawings exemplify a state where the mattress 390M is not provided.

As illustrated in FIG. 16A, in the bed 310B, the frame 390F is attached to a base frame 390B. The back section 70a, the upper leg section 70b, the lower leg section 70c, and the like are provided on the frame 390F. In this example, the seat section 70e is provided. Casters 390C may be provided to the base frame 390B.

As illustrated in FIG. 16A, in the bed device 310, the angle (inclination) of the frame 390F is changeable. The inclination may include, in addition to the front-and-behind inclination, the right-and-left inclination.

As illustrated in FIG. 16B, in the bed device 310, the angle of each of the back section 70a, the upper leg section 70b, and the lower leg section 70c is changeable. The angle of each of the head-right-side side rail 320 and the head-left-side side rail 340 changes in accordance with the change in the angle of the back section 70a. The head-right-side side rail 320 and the head-left-side side rail 340 are tracking type side rails. The state in FIG. 16B corresponds to a cardiac position.

In the example of FIG. 16B, the leg-right-side side rail 330 and the leg-left-side side rail 350 are in an "up state".

As illustrated in FIG. 16C, the leg-right-side side rail 330 and the leg-left-side side rail 350 can be made to be a "down state".

As illustrated in FIGS. 16B and 16C, the height of the bed 310B is changeable. The height corresponds to, for example, a distance between a top surface (for example, a top surface of the section) of the bed 310B and a floor surface.

Figure 17A:
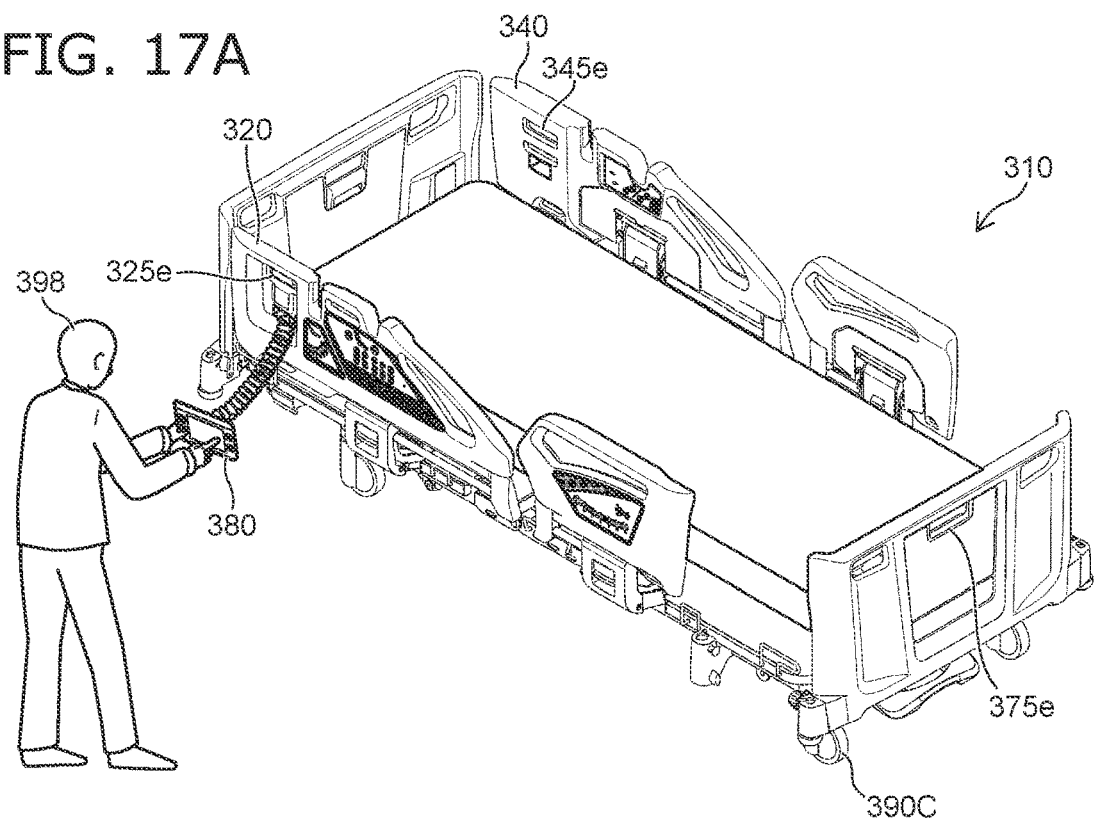
FIGS. 17A and 17B are schematic perspective views exemplifying use states of the bed device according to the embodiment.
Figure 17B:
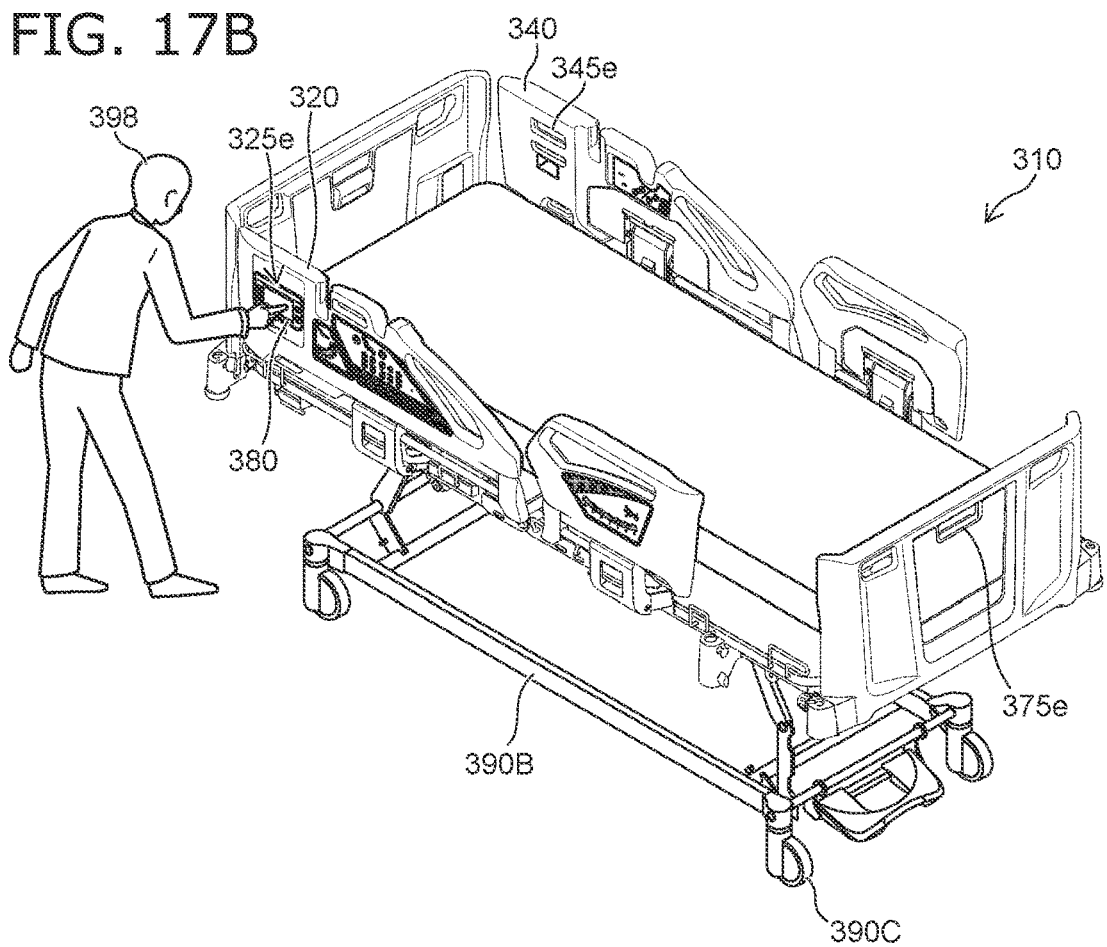

FIGS. 17A and 17B are schematic perspective views exemplifying use states of the bed device according to the embodiment.

FIG. 17A exemplifies a low state of the bed 310B. At this time, a caretaker or the like 398 (for example, a caretaker, a health care worker, or the like) can manipulate the bed manipulation device 380 in a state of being taken out from the hook portion (for example, the through-hole 325e of the head-right-side side rail 320).

FIG. 17B exemplifies a high state of the bed 310B. At this time, the caretaker or the like 398 can manipulate the bed manipulation device 380 in a state of being attached to the hook portion. The bed manipulation device 380 is attached, for example, to three hook portions. The three hook portions are the through-hole 325e of the head-right-side side rail 320, a through-hole 345e of the head-left-side side rail 340, and the through-hole 375e of the foot board 370.

Hereinafter, an example of electric components in the bed device 310 will be described.

Figure 18:
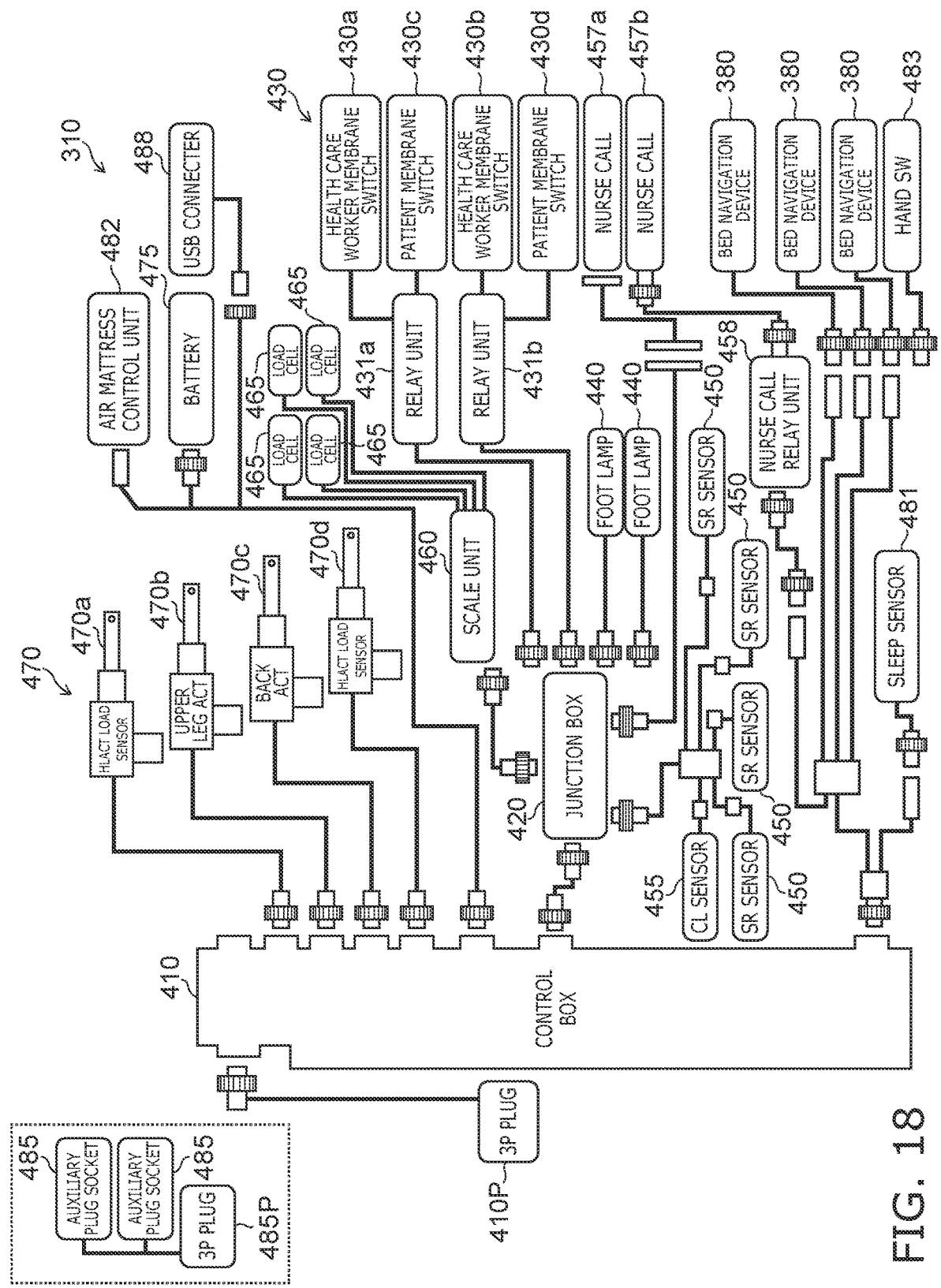
FIG. 18 is a schematic diagram exemplifying the bed device according to the embodiment.

FIG. 18 is a schematic diagram exemplifying the bed device according to the embodiment.

As illustrated in FIG. 18, in the bed device 310, a control box 410 is provided. In addition to this, in the bed device 310, various kinds of devices are provided. The various kinds of devices include a junction box 420, a membrane switch 430, foot lamps 440, side rail sensors 450 (SR sensor), a caster lock sensor 455 (CL sensor), a nurse call 457a, a nurse call 457b, a nurse call relay unit 458, a scale unit 460, load cells 465, an actuator 470, a battery 475, and the like. A part of the various kinds of devices may be omitted.

The control box 410 can be connected to the various kinds of devices. The connection between the control box 410 and the various kinds of devices is made directly or via the junction box 420. The control box 410 controls a bed operation and various kinds of functions. The control box 410 serves as a master of serial communication in the bed device 310.

In the control box 410, a plug 410P (for example, 3-pin plug) is provided. Electric power is supplied from the plug 410P to the control box 410. The electric power is supplied from the control box 410 to the various kinds of instruments.

The junction box 420 relays the connection between the control box 410 and the other various kinds of instruments.

The membrane switch 430 includes health care worker membrane switches 430a and 430b. These membrane switches correspond to the switch units 323 and 343. The membrane switch 430 includes patient membrane switches 430c and 430d. These membrane switches correspond to the switch units 327 and 347. The health care worker membrane switch 430a and the patient membrane switch 430c are connected to the junction box 420 via a relay unit 431a. The health care worker membrane switch 430b and the patient membrane switch 430d are connected to the junction box 420 via a relay unit 431b.

Bed manipulation buttons (switches) are provided to the health care worker membrane switches 430a and 430b. As has already been described, the bed manipulation buttons include a cardiac manipulation button (for example, link manipulation button), an expansion/reverse expansion button, a KIND motion manipulation button (for example, another link manipulation button), a CPR button, a nurse call button, a patient membrane switch prohibition button, an entire switch prohibition button, and the like. By these bed manipulation buttons, the operations having been described related to the switch units 323 and 343 are conducted.

Bed manipulation buttons are provided to the patient membrane switches 430c and 430d. As has already been described, the bed manipulation buttons include the back section manipulation button, the upper leg section manipulation button, and the nurse call button. The patient membrane switches 430c and 430d may include charging terminals and the like.

In the health care worker membrane switches 430a and 430b and the patient membrane switches 430c and 430d, the bed manipulation buttons are provided at positions at the middle in the up-and-down direction. When the bed manipulation button is present in the lower portion, the manipulation is difficult to be conducted. When the bed manipulation button is present in the upper portion, the manipulation may be erroneously conducted. The bed manipulation buttons are present at positions at the middle in the up-and-down direction to make the manipulation easy and to allow the erroneous manipulation to be prevented.

Foot lamp buttons correspond to the switches 323q and 343q. When the foot lamp button is pressed, the foot lamp 440 lights on. The foot lamps 440 conduct illumination from an end portion of the bed 310B to a floor surface. One foot lamp 440 is provided to each of right and left sides of the bed 310B, for example. The foot lamps 440 are provided, for example, to right-and-left end portions at a rear side (lower side) of the seat section 70e. The foot lamps 440 may be provided to other portions, such as the back section 70a, the upper leg section 70b, the lower leg section 70c (see FIG. 16B, and the like), and the like. For example, each time when the foot lamp buttons (switches 323q and 343q) are pressed, in the foot lamps 440, lighting-out→lighting-up dark→lighting-up bright→lighting-out are repeatedly conducted. For example, the foot lamps 440 are lit up by the health care worker. For example, in a case where the user frequently goes to a toilet and other cases, the foot lamps 440 light up by the health care worker before the user goes to bed. For example, in a case where bed-leaving is detected, a case where nurse call has occurred, or other cases, the foot lamps 440 are lit up by the health care worker.

For example, when the user of the bed 310B leaves the bed during the night for going to a toilet and the like, the foot lamps 440 are lit up. At this time, the inside of the room is dark in many cases. The foot lamps 440 suddenly light up bright to cause inconvenience to a person who is sleeping in the surrounding. The lighting-up dark at the beginning prevents the inconvenience.

The side rail sensor 450 detects whether each side rail is raised. The four side rail sensors 450 are provided. The four side rail sensors 450 include a head-right-side side rail sensor, a head-left-side side rail sensor, a leg-right-side side rail sensor, and a leg-left-side side rail sensor. A detection result is displayed, for example, on a terminal in a nurse station. The detection result may be displayed on the bed manipulation device 380. Warning sound may occur based on the detection result. As the side rail sensor 450, for example, a magnetic sensor, a barometric pressure sensor, or the like is used. As the side rail sensor 450, another sensor may be used.

The caster lock sensor 455 detects whether the casters 390C are locked. As the caster lock sensor 455, for example, a magnetic sensor is used. For example, in the caster 390C, a bar or the like that is linked with lock or lock cancel of the caster 390C is provided. By detecting a state of the bar, a lock state of the caster 390C can be detected. A detection result by the caster lock sensor 455 is displayed, for example, on the terminal in the nurse station. The detection result may be displayed on the bed manipulation device 380. Warning sound may occur based on the detection result by the caster lock sensor 455.

The nurse call 457a is connected to the junction box 420. The nurse call 457b is connected to the nurse call relay unit 458. The nurse call relay unit 458 can attain cooperation with the nurse call (for example, the nurse call 457b) that is provided to a hospital and a facility. The nurse calls 457a and 457b are nurse calls of domestic or foreign manufacture. For example, the nurse call 457a is of foreign manufacture. For example, the nurse call 457b is of domestic manufacture.

The load cells 465 are provided to four corner portions of the bed 310B. The four load cells 465 are used. The body weight of the user can be measured by the load cells 465 and the scale unit 460.

The actuator 470 includes a height change actuator 470a ("HLACT"), an actuator 470b for the upper leg section 70b ("upper leg ACT"), an actuator 470c for the back section 70a ("back ACT" with CPR), a height change actuator 470d ("HLACT"), and the like. Each of the actuator 470a and 470d includes a load sensor.

In one example, the actuator 470c for the back section 70a includes a mechanical mechanism (hereinafter, referred to as a manual CPR mechanism) for manually conducing the lowering operation. With the manual CPR mechanism, the back section 70a can be manually lowered during an emergency. For example, a dedicated lever or the like is provided, and this lever is manipulated, so that it is possible to manually lower the back section 70a, and obtain a posture for CPR. For example, a brake plate of the actuator 470c for the back section 70a can be manually slid. This cancels the brake of the actuator 470c, and the back section 70a is lowered by the force of gravity.

The actuator 470 serves as a drive source that adjusts the movable part that is included in the bed 310B. The actuator 470 operates the movable part via the coupling part by the operation of a telescopic rod. A position sensor is provided to each of the actuators. The control box 410 reads out position information. Movement (for example, including bed-leaving) of the user (patient, or the like) on the bed 310B may be determined by the load sensor of the actuator 470.

The battery 475 supplies electric power during power failure, during transport of the bed 310B, and the like. A desired operation can be obtained even in a status where no electric power is supplied. A selector switch as to whether charging to the battery 475 is conducted or not may be provided. Charging may be possible, independent of the state of the selector switch, in a state where electric power (AC power supply) is supplied to the bed 310B.

For example, when the bed device 310 is driven by the AC power supply, electric power is supplied, from the control box 410, to the battery 475, an air mattress control unit 482, and a USB charger 488 (see FIG. 18). When no electric power is supplied from the AC power supply, electric power is supplied, from the battery 475, to the control box 410, the air mattress control unit 482, and the USB charger 488. In a case where no electric power is supplied from the AC power supply and no electric power is supplied from the battery 475, the bed 310B does not operate.

As illustrated in FIG. 18, in the bed device 310, a sleep sensor 481, the air mattress control unit 482, and the bed manipulation device 380 are provided. In the bed device 310, a hand switch 483 may be provided.

The sleep sensor 481 measures a sleep status of the user (patient, or the like) of the bed 310B. In a case where the bed manipulation device 380 is provided, a measurement result of the sleep status and a sleep history may be output (for example, displayed) to the bed manipulation device 380.

For example, a connector for the air mattress control unit 482 is provided to the control box 410. In the air mattress, a link operation in association with a posture of the bed 310B may be conducted. The link operation may vary depending on the type of the air mattress. The bed manipulation device 380 may conduct the setting of and the change in the operation of the air mattress.

In the bed device 310, auxiliary plug sockets 485 are further provided. In this example, the two auxiliary plug sockets 485 are provided. The auxiliary plug socket 485 is a plug receptacle device. The auxiliary plug socket 485 includes a plug 485P. The plug 485P is a plug that is compliant with medical standards. The plug 485P is a 3-pin plug. The plug 485P is provided separately from the plug 410P of the control box 410.

The bed device 310 may include the USB charger 488 (see FIG. 18). The USB charger 488 corresponds to the USB terminal 327u (or 347u). The USB charger 488 conducts power feeding to an instrument corresponding to the USB charging. The number of ports of the USB charger 488 may be one. The output rating of the USB charger 488 is DC5V/1A. A port is provided to the patient membrane switch 430c on the right-side side rail.

The bed device 310 may include an error display LED. The error display LEDs correspond to the displays 323t and 343t.

In the bed device 310, bed-leaving of the user of the bed 310B may be detected. For example, the load cell 465 detects bed-leaving. For example, the load sensor that is built-in the actuator detects bed-leaving. Information related to bed-leaving is transmitted to the nurse call system, and is output to the terminal of the nurse station. Information related to bed-leaving may be output to the bed manipulation device 380. The output of the information related to bed-leaving may include, for example, a visual stimulus such as a lamp or an auditory stimulus such as warning sound.

Hereinafter, an example of the bed manipulation device 380 will be described.

The bed manipulation device 380 is connected to the bed 310B. In the bed manipulation device 380, the setting related to the bed 310B can be conducted, and the display is conducted. The language of the display in the bed manipulation device 380 is selectable. For example, display using Japanese, English, Chinese, or Portuguese is possible. The bed manipulation device 380 is attached, for example, to the right-and-left side rails or the foot board 370.

The maximum number of the bed manipulation devices 380 that are provided to the bed device 310 is three, for example. In one example, one bed manipulation device 380 or one hand switch 483 (which is described later) is connected to the bed 310B. In another example, one bed manipulation device 380 and one hand switch 483 are connected to the bed 310B. In still another example, two bed manipulation devices 380 are connected to the bed 310B. In still another example, two bed manipulation devices 380 and one hand switch 483 are connected to the bed 310B. In still another example, three bed manipulation devices 380 are connected to the bed 3108.

Figure 19A:
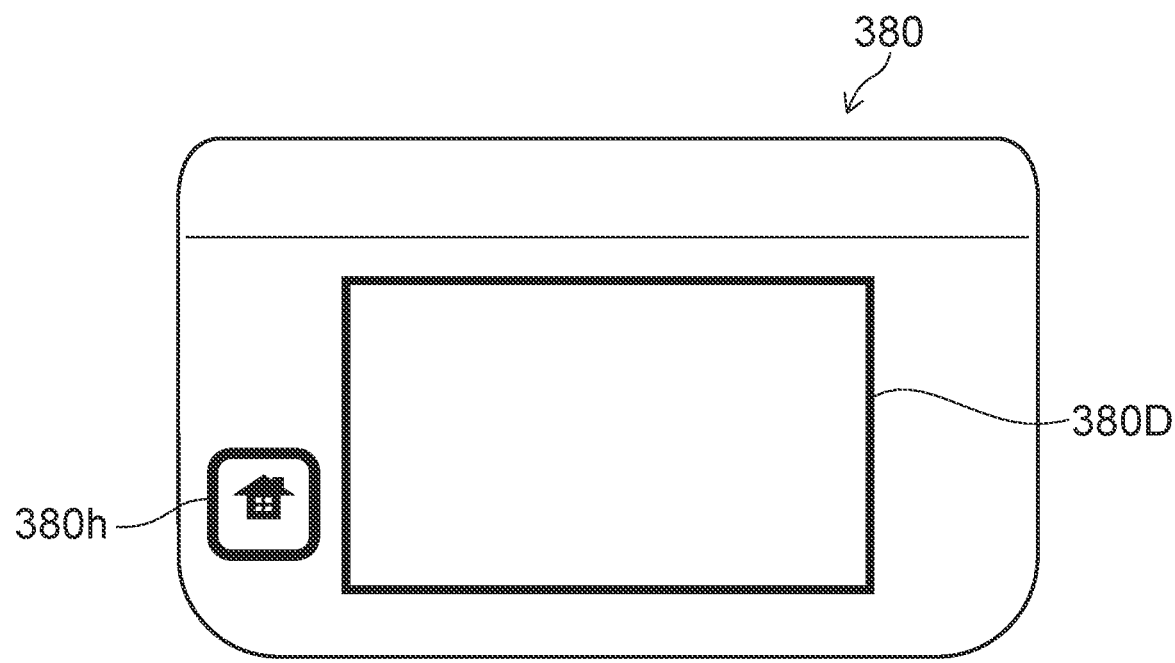
FIGS. 19A and 19B are schematic diagrams partially exemplifying the bed device according to the embodiment.
Figure 19B:
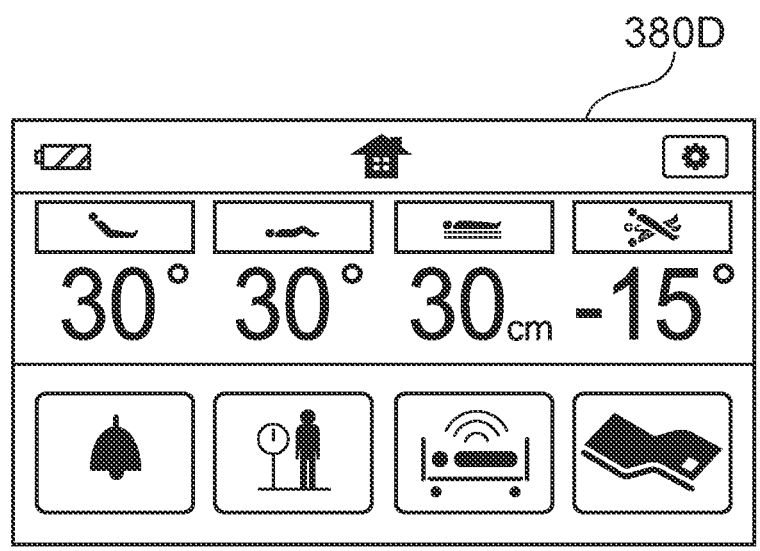

FIGS. 19A and 19B are schematic diagrams partially exemplifying the bed device according to the embodiment.

FIG. 19A exemplifies the bed manipulation device 380 that is provided mainly to the head-side side rail (head-right-side side rail 320 or the head-left-side side rail 340). The bed manipulation device 380 includes a display input unit 380D. A home button 380h is provided to the bed manipulation device 380.

As illustrated in FIG. 19B, various kinds of displays are capable of being displayed on the display input unit 380D. The display input unit 380D allows the display of a posture of the bed 310B and a body weight of the user. The display input unit 380D allows a setting of a bed-leaving sensor. The display input unit 380D allows the display related to the sleep sensor 481. The display input unit 380D allows the manipulation of the air mattress. The display input unit 380D allows the display of an error.

Figure 20A:
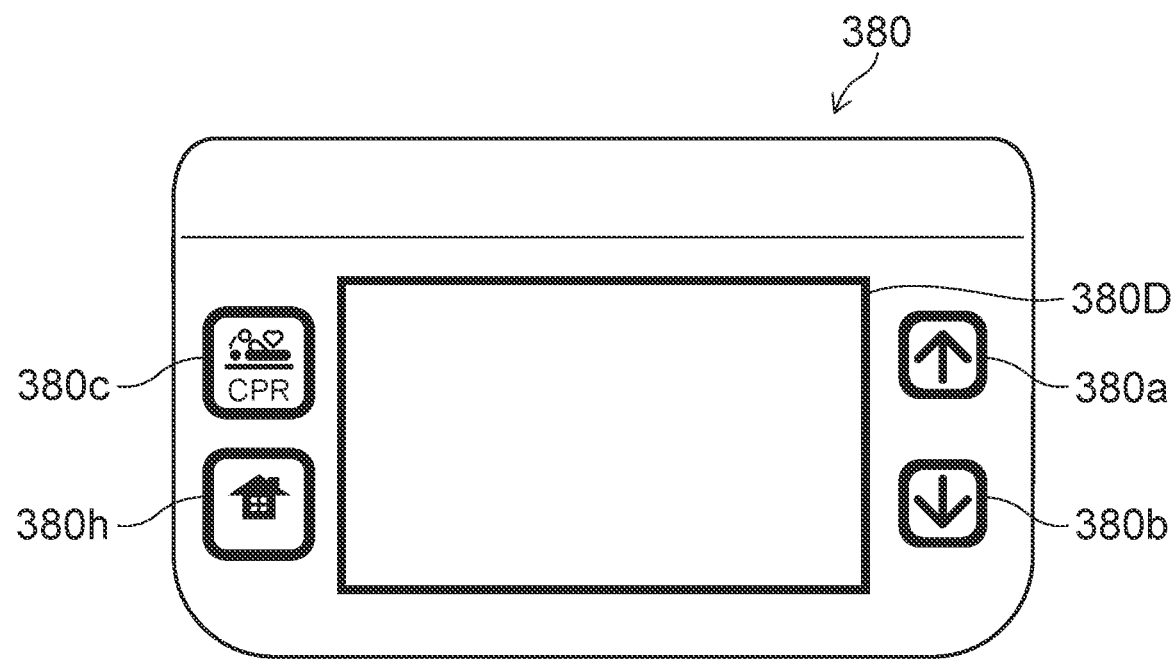
FIGS. 20A and 20B are schematic diagrams partially exemplifying the bed device according to the embodiment.
Figure 20B:
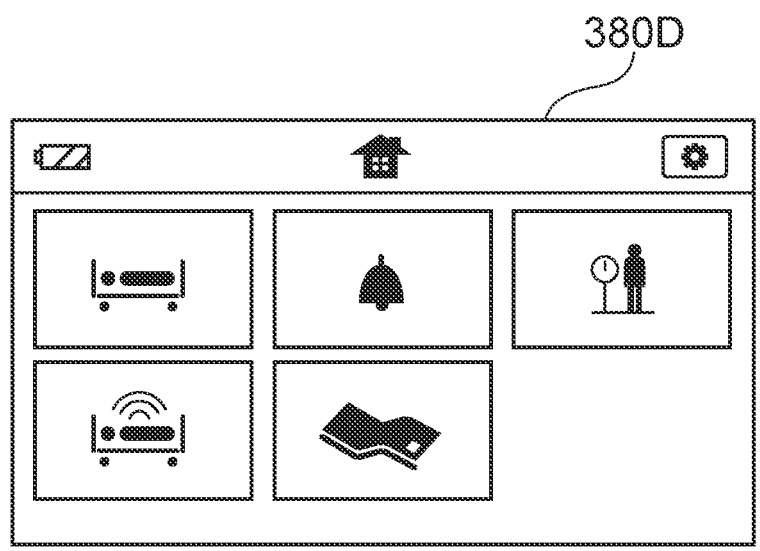

FIGS. 20A and 20B are schematic diagrams partially exemplifying the bed device according to the embodiment.

FIG. 20A exemplifies the bed manipulation device 380 that is provided mainly to the foot board 370. The bed manipulation device 380 includes the display input unit 380D. In addition to the home button 380h, a raising button 380a, a lowering button 380b, and a CPR button 380c are provided to the bed manipulation device 380. With the raising button 380a or the lowering button 380b, the movable part of the bed 310B is raised or lowered. A posture for CPR is attained by the CPR button 380c.

As illustrated in FIG. 20B, various kinds of displays are capable of being displayed on the display input unit 380D. The display input unit 380D allows the manipulation of the bed 310B. The bed manipulation includes, for example, a cardiac operation, an inclination operation, a link operation (KIND operation), back raising/lowering, upper leg raising/lowering, height raising/lowering, and the like. The display input unit 380D allows the display of a body weight of the user. The display input unit 380D allows the bed-leaving sensor to be set. The display input unit 380D allows a display related to the sleep sensor 481. The display input unit 380D allows the manipulation of the air mattress. The display input unit 380D allows the display of an error.

Hereinafter, an example of the hand switch 483 will be described.

Figure 21:
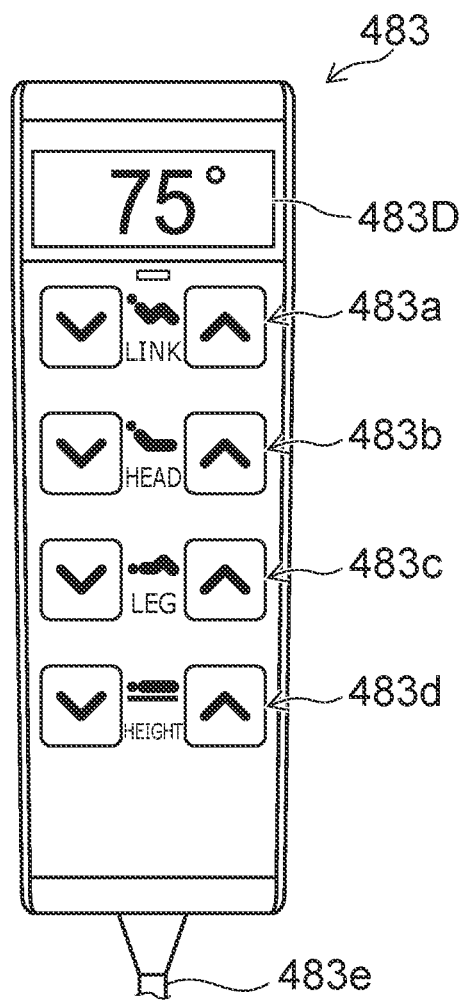
FIG. 21 is a schematic diagram partially exemplifying the bed device according to the embodiment.

FIG. 21 is a schematic diagram partially exemplifying the bed device according to the embodiment.

FIG. 21 exemplifies the hand switch 483. The hand switch 483 includes switch pairs 483a to 483d. The switch pair 483a includes switches for raising or lowering related to a "link" operation. The switch pair 483b includes switches for raising or lowering related to a "back raising" operation. The switch pair 483c includes switches for raising or lowering related to a "leg raising" operation. The switch pair 483d includes switches for raising or lowering related to a "height" change operation.

The angle or the height may be displayed on a display 483D of the hand switch 483. The hand switch 483 is connected, for example, to the control box 410 with a cable 483e or the like.

Hereinafter, an example of the auxiliary plug socket 485 will be described.

Figure 22:
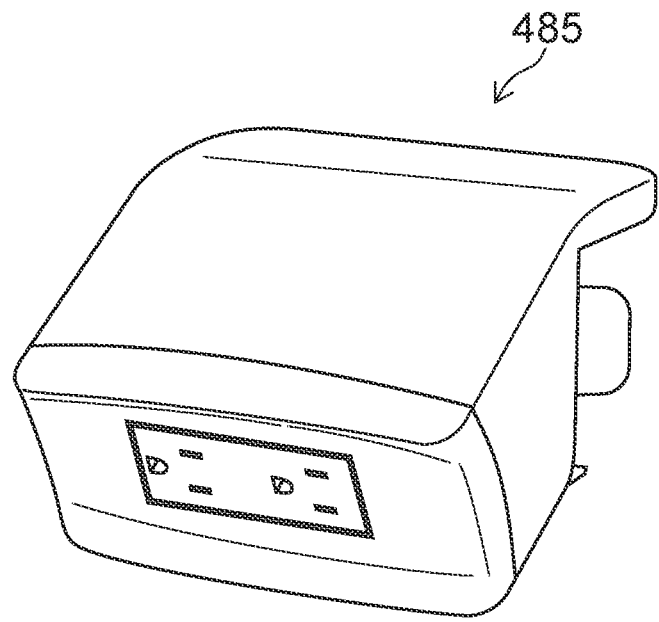
FIG. 22 is a schematic perspective view partially exemplifying the bed device according to the embodiment.

FIG. 22 is a schematic perspective view partially exemplifying the bed device according to the embodiment.

FIG. 22 exemplifies the auxiliary plug socket 485 (for example, plug receptacle device). Plugs of electronic instruments that are used in the periphery of the bed 310B are connectable to the auxiliary plug socket 485. As has already been described, the plug 485P of the auxiliary plug socket 485 is provided separately from the plug 410P of the control box 410. The auxiliary plug socket 485 includes two pairs of plug receptacles (outlet holes of the plug). The two pairs of plug receptacles are arranged from side to side.

Figure 23:
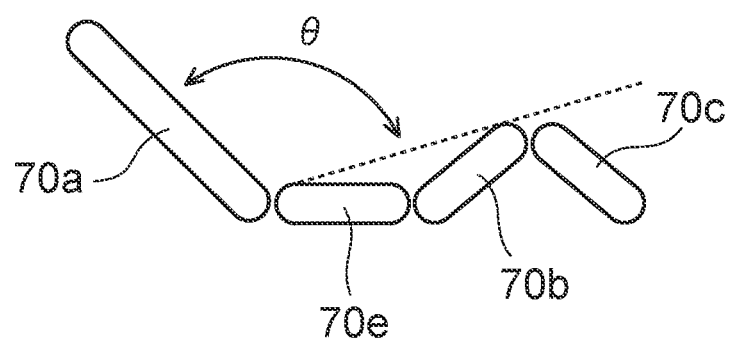
FIG. 23 is a schematic diagram partially exemplifying the bed device according to the embodiment.

FIG. 23 is a schematic diagram partially exemplifying the bed device according to the embodiment.

FIG. 23 exemplifies the back section 70a, the upper leg section 70b, the lower leg section 70c, and the seat section 70e. The angle of each of the back section 70a, the upper leg section 70b, and the lower leg section 70c is changeable. The control is conducted such that an angle between the sections does not become a predetermined value (for example, 90 degrees) or lower. For example, the control is conducted such that a angle between a line (dashed line in FIG. 23) connecting a lower end of the back section 70a and an upper end of the upper leg section 70b, and the back section 70a becomes a predetermined value (for example, 90 degrees) or lower. For example, the angle is made to be a predetermined value or lower by the control (link) of any motion in the plurality of sections.

The operation angle of the back section 70a is, for example, 0 degree to 70 degrees. The operation angle of the upper leg section 70b is 0 degree or higher and 25 degrees or lower. The operation range of the "height" is, for example, 43 cm. The floor height may vary depending on the bed frame. The range of the floor height is, for example, 30 cm to 73 cm, 32.5 cm to 75.5 cm, or 35 cm to 78 cm.

The operation angle of the inclination of the section is −15 degree to 15 degree. For example, in order to avoid interference in the bed frame, after the height has been adjusted to the height of "minimum floor height+3 cm", the inclination operation is conducted.

The operations to the cardiac position and the section flat are accompanied with the inclination operation. In these operations, an operation sequence by taking the slide of the user into consideration is applied.

In the motorized CPR operation, the operation is conducted in the following order. When simultaneous operations are possible, the simultaneous operations may be conducted. In the motorized CPR operation, firstly, the stroke of the actuator 470c for the back section 70a ("back ACT") is operated to the lower limit. Within 30 seconds after the button for the motorized CPR operation is pressed, the actuator 470c reaches the lower limit. Thereafter, the inclination operation is conducted, and the inclined angle becomes 0 degree. Thereafter, the height is adjusted, and the height becomes the minimum floor height. The minimum floor height is, for example, a "temporal stop height". Thereafter, the operation of causing the upper leg section 70b to be 0 degree is conducted.

In the bed device 310, the manipulation by the bed manipulation device 380 can cause button operations related to various kinds of operations to be in a "manipulation prohibition" state.

Figure 24A:
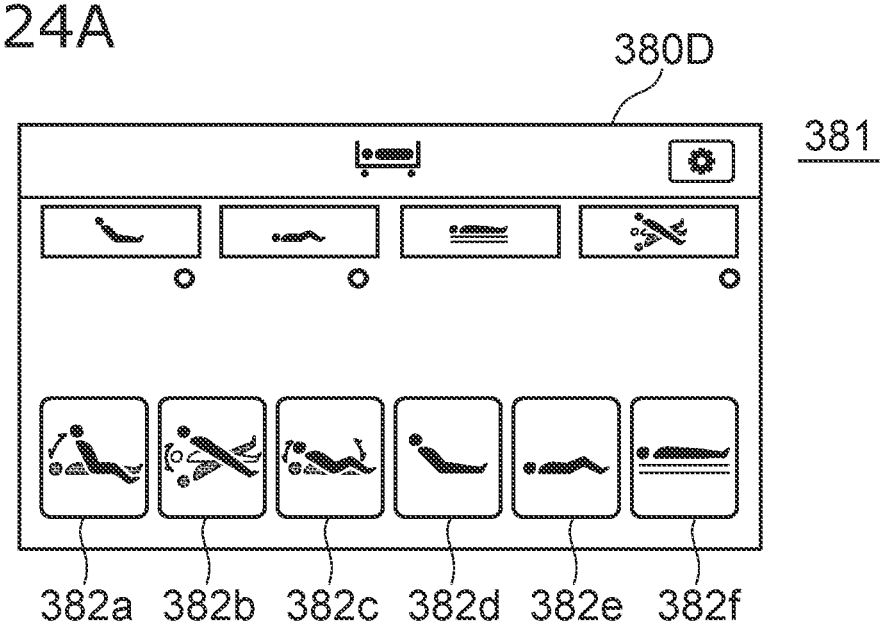
FIGS. 24A and 24B are schematic diagrams partially exemplifying the bed device according to the embodiment.
Figure 24B:
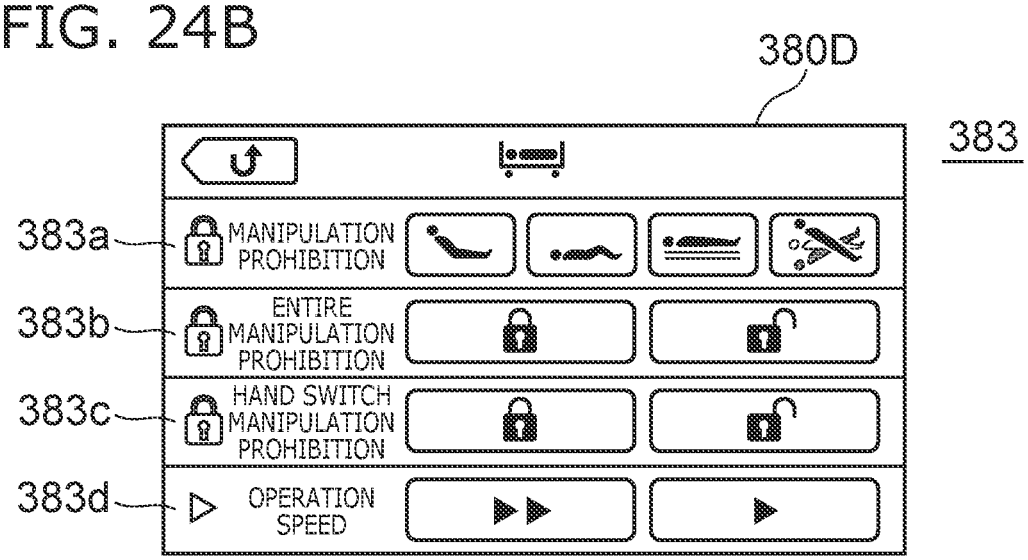

FIGS. 24A and 24B are schematic diagrams partially exemplifying the bed device according to the embodiment.

These drawings exemplify the display input unit 380D of the bed manipulation device 380. FIG. 24A exemplifies a case where the display input unit 380D is a bed manipulation screen 381. FIG. 24B exemplifies a case where the display input unit 380D is an actuator individual manipulation prohibition screen 383 (bed setting screen).

As illustrated in FIG. 24A, for example, buttons 382a to 382f and the like are provided. These buttons are, for example, an input reception region in a touch-type input device. These buttons are touched to conduct the bed manipulation. With the button 382a, the cardiac operation is conducted. With the button 382b, the inclination operation is conducted. With the button 382c, the link operation ("KIND operation") is conducted. With the button 382d, the back operation (change in the back angle) is conducted. With the button 382e, the upper leg operation (change in the upper leg angle) is conducted. With the button 382f, the height operation (change in the height) is conducted. For example, in a case where the back of the bed 310B is raised, when the button 382d is pressed and the raising button 380a is thereafter pressed, the bed 310B moves. The bed 310B moves during a period when the raising button 380a is being pressed. For example, in a case where the height of the bed is lowered, when the button 382f is pressed and the lowering button 380b is thereafter pressed, the height of the bed 310B is lowered during a period when the lowering button 380b is being pressed.

As illustrated in FIG. 24B, the display input unit 380D can be shifted to the actuator individual manipulation prohibition screen 383 (bed setting screen). The manipulation in a display input region 383a can attain individual manipulation prohibition of each of the back operation, the upper leg operation, the height operation, and the inclination operation. The manipulation in a display input region 383b can attain entire manipulation prohibition or cancel manipulation prohibition. The manipulation in a display input region 383c can prohibit the manipulation of the hand switch 483 or cancel the manipulation prohibition.

For example, in a case of manipulation prohibition for the back operation, the cardiac operation, the link operation, and the back operation are prohibited. For example, in a case of manipulation prohibition for the upper leg operation, the cardiac operation, the link operation, and the upper leg operation are prohibited. For example, in a case of manipulation prohibition for the height operation, the cardiac operation, the inclination operation, and height operation are prohibited. For example, in a case of manipulation prohibition for the inclination operation, the cardiac operation and the inclination operation are prohibited.

In one example, "entire manipulation prohibition" is possible. In another example, "manipulation prohibition" may be selectively (individually) applied to the actuator 470 (470a to 470d (see FIG. 18), and the like). The bed manipulation device 380 cancels the "manipulation prohibition" on the actuator 470.

In a case where the bed manipulation device 380 is taken out from the bed 310B, a case where the cable for the connection of the bed manipulation device 380 is disconnected, and other cases, the selective "manipulation prohibition" on the actuator 470 cannot be canceled. In this case, the "entire manipulation prohibition" is canceled to allow the "manipulation prohibition" on the actuator 470 to be canceled.

The manipulation prohibition on the actuator 470, the manipulation prohibition on the hand switch 483, or the "entire manipulation prohibition" is independently managed. For example, in a case of the individual manipulation prohibition on the actuator 470, when the "entire manipulation prohibition" is made and the "entire manipulation prohibition" is canceled thereafter, the individual manipulation prohibition on the actuator 470 remains.

When a button set to the prohibition is pressed, buzzer sound rings, and prohibition LEDs (for example, the displays 323t and 343t, and the like) of the membrane switches blink on and off. When no buzzer sound rings, it cannot be understood whether the button is prohibited or broken. When buzzer sound rings, it can be understood that the button is prohibited.

When a button set to the prohibition in the hand switch 483 is pressed, the hand switch 483 sounds. When a button set to the prohibition in the membrane switch is pressed, for example, the junction box 420 sounds.

The manipulation of the health care worker membrane switch or the bed manipulation device 380 can cause the patient membrane switch and the hand switch 483 to be in a manipulation prohibition state. The manipulation prohibition is capable of being canceled when the health care worker membrane switch or the bed manipulation device 380 is comprised.

The manipulation of the health care worker membrane switch or the bed manipulation device 380 can prohibit the entire manipulation ("entire manipulation prohibition"). The manipulation prohibition is capable of being canceled when either of the health care worker membrane switch and the bed navigation device is comprised.

For example, in a case where the bed manipulation device 380 is not connected to the bed 310B, a case of a partial failure (communication failure), and other cases, the "entire manipulation prohibition" is canceled. In this case, for example, the manipulation is possible by the hand switch 483. When the user is not caused to manipulate, the hand switch 483 may be taken out. When a button set to the prohibition is pressed, buzzer sound rings, and a prohibition LED of the membrane switch blinks on and off.

When a button for the "entire manipulation prohibition" is pressed in a manipulation prohibition state of the hand switch 483, the "entire manipulation prohibition" is made. When the "entire manipulation prohibition" is thereafter pressed, the manipulation prohibition on the hand switch 483 and the entire manipulation prohibition are canceled. In the "entire manipulation prohibition", the CPR operation is conducted. In any case of the "manipulation prohibition", the "hand switch manipulation prohibition", and the "entire manipulation prohibition", the CPR operation is conducted.

For example, in the "current setting", in a case where the hand switch 483 is not manipulation prohibition and the "entire manipulation prohibition" is not set, when a button of the manipulation prohibition on the hand switch 483 is pressed, the hand switch 483 becomes the manipulation prohibition, while the "entire manipulation" is not manipulation prohibition (canceled state).

For example, in the "current setting", in a case where the hand switch 483 is not manipulation prohibition and the "entire manipulation prohibition" is not set, when a button for the "entire manipulation prohibition" is pressed, the hand switch 483 and the entire manipulation are prohibited.

For example, in the "current setting", in a case where the hand switch 483 is manipulation prohibition and the "entire manipulation prohibition" is not set, when a button for the manipulation prohibition on the hand switch 483 is pressed, the hand switch 483 is not manipulation prohibition (canceled state), and the "entire manipulation" is not manipulation prohibition (canceled state).

For example, in the "current setting", in a case where the hand switch 483 is manipulation prohibition and the "entire manipulation prohibition" is not set, when a button for the "entire manipulation prohibition" is pressed, the hand switch 483 and the entire manipulation are prohibited.

For example, in the "current setting", in a case where the hand switch 483 is manipulation prohibition and the "entire manipulation prohibition" is set, when a button for the manipulation prohibition on the hand switch 483 is pressed, the hand switch 483 and the entire manipulation are prohibited.

For example, in the "current setting", in a case where the hand switch 483 is manipulation prohibition and the "entire manipulation prohibition" is set, when a button for the "entire manipulation prohibition" is pressed, the manipulation prohibition of the hand switch 483 is canceled (canceled state) and the entire manipulation prohibition is canceled (canceled state).

The manipulation in a display input region 383*d* exemplified in FIG. 24B can change the operation speed. For example, the speed of the various operations is changeable in a plurality of stages (for example, two stages, and the like).

A history related to various kinds of operations by the bed device 310 may be stored. For example, a history is stored in a memory in the control box 410 or the like. The memory in which the history is stored may be provided in the junction box 420, the hand switch 483, or the like. The memory in which the history is stored may be provided in the bed manipulation device 380. Information related to the history is not reset by on/off of the power supply. The information related to the history includes, for example, an operation history of the control box 410, an operation history of the actuator 470, an operation history of the hand switch 483, a manipulation content history, a failure history, and a bed-leaving/presence-in-bed history.

The embodiments include, for example, the following configurations.

(Configuration 1)

A control device including a controller that controls a speed of the extension/contraction of the axis of the first actuator based on a first changing amount of extension/contraction of an axis of a first actuator of a bed device.

(Configuration 2)

The control device according to Configuration 1, in which the first actuator can move a first movable part, and a second changing amount of the first movable part having moved due to a change in the extension/contraction of the axis of the first actuator is predetermined.

(Configuration 3)

The control device according to Configuration 2, in which the bed device further includes a first coupling part, the first coupling part is coupled to the first movable part and the first actuator, and the first coupling part generates a motion of the first movable part in accordance with the change in the extension/contraction of the axis of the first actuator.

(Configuration 4)

A control device including a controller, a bed device including a first movable part and a first actuator that moves the first movable part, the controller controlling the first actuator based on first relation information related to a relation between a first changing amount of a motion of the first actuator and a second changing amount of a motion of the first movable part.

(Configuration 5)

The control device according to Configuration 4, in which the controller controls the first actuator such that a first speed of the motion of the first movable part during a period excluding a motion start and a motion end of the first movable part is substantially constant.

(Configuration 6)

The control device according to Configuration 4 or 5, further including an acquisition unit that acquires the first relation information, in which the controller controls the first actuator based on the first relation information acquired by the acquisition unit.

(Configuration 7)

The control device according to any one of Configurations 4 to 6 further including a memory that stores therein the first relation information.

(Configuration 8)

The control device according to any one of Configurations 4 to 7, in which the bed device further includes a first coupling part, the first coupling part is coupled to the first movable part and the first actuator, and the first coupling part generates the motion of the first movable part in accordance with the motion of the first actuator.

(Configuration 9)

The control device according to any one of Configurations 4 to 8, in which the first actuator extends/contracts or rotates, and the controller controls the first actuator based on first state information related to a state of the extension/contraction or the rotation of the first actuator and the first relation information.

(Configuration 10)

The control device according to any one of Configurations 4 to 9, in which the bed device further includes a second movable part and a second actuator, the second actuator is capable of moving the second movable part, and the controller controls the second actuator.

(Configuration 11)

The control device according to Configuration 10, in which the controller controls the second actuator based on second relation information related to a relation between a third changing amount of the motion of the second actuator and a fourth changing amount of a motion of the second movable part.

(Configuration 12)

The control device according to Configuration 10 or 11, in which the controller controls the second actuator such that a second speed of the motion of the second movable part is substantially constant in a period excluding the start motion and the end motion of the second movable part.

(Configuration 13)

The control device according to any one of Configurations 10 to 12, in which the second actuator extends/contracts or rotates, and the controller controls the second actuator based on second state information related to a state of the extension/contraction or the rotation of the second actuator and the second relation information.

(Configuration 14)

The control device according to Configuration 12, in which the controller controls the motion of the first actuator such that a first speed of the motion of the first movable part during a period excluding a motion start and a motion end of the first movable part is substantially constant, and, the first speed is substantially identical with the second speed.

(Configuration 15)

The control device according to any one of Configurations 10 to 14, in which the bed device further includes a second coupling part, the second coupling part is coupled to the second movable part and the second actuator, and the second coupling part generates a motion of the second movable part in accordance with a motion of the second actuator.

(Configuration 16)

A bed device including the control device according to any one of Configurations 2 to 15; the first movable part: and the first actuator.

According to the embodiments, a control device and a bed device capable of more adequately controlling the motion of the movable part can be provided.

In the foregoing, the embodiments have been described with reference to the specific examples. However, the embodiments are not limited to these specific examples. For example, the specific configurations of the elements included in the bed device, such as the control device, the controller, the acquisition unit, the memory, the movable part, the actuator, and the detector, can be included in the scope of the present embodiment, as long as those skilled in the art can similarly implement the embodiments by the appropriate selection from the publicly known range, and obtain the similar effects.

The combination of any two or more elements in the specific examples within a technically possible range is included in the scope of the present embodiment as long as the gist of the present embodiment is included.

In addition, all the bed devices that can be implemented through the design changes as appropriate by those skilled in the art based on the bed devices described above as the embodiments belong to the scope of the present embodiment as long as the gist of the present embodiment is included.

In addition, within the spirit of the present embodiment, those skilled in the art can conceive of various changes and modifications, and it is understood that these changes and modifications also belong to the scope of the present embodiment.

REFERENCE SIGNS LIST

40 controller, 40A control circuit, 401 acquisition unit, 40M memory, 70 bed, 70B bed frame, 70M movable part, 70a back section, 70b upper leg section, 70c lower leg section, 70e seat section, 71, 72 first actuator, second actuator, 71M, 72M first movable part, second movable part, 71R, 72R first coupling part, second coupling part, 71S, 72S first detector, second detector, 71d, 72d difference, 73a back actuator, 73aS back detector, 73b upper leg actuator, 73bS upper leg detector, 75B base frame, 75c caster, 78A headboard, 78B foot board, 78C, 78D side rail, 78M mattress, 90 control device, ΔH1, ΔH2, changing amount, 110 bed device, AA arrow, H1, H2 first, second height, R, R1,R2 state, S1 to S4 first to fourth control signal, SA, SM speed, p1 to p3 period, t1 to t4 time, tm time, 310 bed device, 310B bed, 320 head-right-side side rail, 320F outer surface, 320G inner surface, 323 switch unit, 323a to 323q switch, 323r to 323t display, 324 angle meter, 324a display, 325a protruding portion, 325b recessed portion, 325c head-side protruding portion, 325d head-side recessed portion, 325e through-hole, 325f lower through-hole, 325g handrail, 325h through-hole, 327 switch unit, 327a to 327d switch, 327n switch, 327u USB terminal, 328 recessed portion, 328h hole, 330 leg-right-side side rail, 330F outer surface, 330G inner surface, 334 angle meter, 334a display, 335f lower through-hole, 335g hand rail, 335h through-hole, 340 head-left-side side rail, 340F outer surface, 340G inner surface, 343 switch unit, 343a to 343q switch, 343r to 343t display, 344 angle meter, 344a display, 345e through-hole, 347 switch unit, 347a to 347d switch, 347n switch, 347u terminal, 350 leg-left-side side rail, 350F outer surface, 350G inner surface, 354 angle meter, 354a display, 355g hand rail, 360 headboard, 370 foot board, 370F outer surface, 370G inner surface, 375e through-hole, 380 bed manipulation device, 380D display input unit, 380a raising button, 380b lowering button, 380c CPR button, 380h home button, 381 bed manipulation screen, 382a to 382f button, 383 actuator individual manipulation prohibition screen, 383a to 383d display input region, 390B base frame, 390C caster, 390F frame, 390M mattress, 398 caretaker or the like, 410 control box, 410P plug, 420 junction box, 430 membrane switch, 430a, 430b health care worker membrane switch, 430c, 430d patient membrane switch, 431a, 431b relay unit, 440 foot lamp, 450 side rail sensor, 455 caster lock sensor, 457a, 457b nurse call, 458 nurse call relay unit, 460 scale unit, 465 load cell, 470 actuator, 470a to 470d actuator, 475 battery, 481 sleep sensor, 482 air mattress control unit, 483 hand switch, 483D display, 483a to 483d switch pair, 483e cable, 485 auxiliary plug socket, 485P plug, 488 charger

The invention claimed is:

1. A control device of a bed device comprising:
a controller comprising a circuit configured to control a first speed of an extension/contraction of a first actuator that controls a first movable part of the bed device and a second speed of an extension/contraction of a second actuator that controls a second movable part of the bed device, based on a first changing amount of extension/contraction of the first actuator and a second changing amount of extension/contraction of the second actuator, so as to maintain a surface of the bed device in a horizontal state when the controller is configured to control the first actuator and the second actuator to lift or lower the surface of the bed device,
wherein
each of the first and second actuators includes an extendable rod and a drive source connected to the extendable rod respectively,
a difference between a maximum length and a minimum length of the extendable rod of the first actuator is different from a difference between a maximum length and a minimum length of the extendable rod of the second actuator, the circuit of the controller controls the first and second actuators so that a speed of a motion of the first movable part and a speed of a motion of the second movable part are substantially identical, thereby maintaining the surface of the bed device in the horizontal state during operation of the first and second actuators, and one of the first actuator and the second actuator has different speed from the other in changing amount of extension/contraction of actuators.

2. The control device according to claim 1, wherein a second changing amount of the first movable part having moved due to the change in the extension/contraction of the axis of the first actuator is predetermined.

3. The control device according to claim 2, wherein the bed device further includes a first coupling part, the first coupling part is coupled to the first movable part and the first actuator, and the first coupling part generates a motion of the first movable part in accordance with the change in the extension/contraction of the axis of the first actuator.

4. The control device according to claim 1, the first movable part is at a head side of a bed frame, the second movable part is at a foot side of the bed frame, and the first actuator has longer difference between the maximum length and the minimum length than the second actuator.

5. A control device comprising:

a controller comprising a circuit, and a bed device including a first movable part and a first actuator that moves the first movable part, and a second movable part and a second actuator that moves the second movable part, the circuit of the controller controlling the first actuator based on first relation information related to a relation between a first changing amount of a motion of the first actuator and a second changing amount of a motion of the first movable part, so as to maintain a surface of the bed device in a horizontal state when the controller is configured to control the first actuator and the second actuator to lift or lower the surface of the bed device, wherein each of the first and second actuators includes an extendable rod and a drive source connected to the extendable rod respectively, a difference between a maximum length and a minimum length of the extendable rod of the first actuator is different from a difference between a maximum length and a minimum length of the extendable rod of the second actuator, the circuit of the controller controls the first and second actuators so that a speed of the motion of the first movable part and a speed of a motion of the second movable part are substantially identical, thereby maintaining the surface of the bed device in the horizontal state during operation of the first and second actuators, and one of the first actuator and the second actuator has different speed from the other in changing amount of extension/contraction of actuators.

6. The control device according to claim 4, wherein the circuit of the controller controls the first actuator such that a first speed of the motion of the first movable part during a period excluding a motion start and a motion end of the first movable part is constant.

7. The control device according to claim 4, further comprising an acquisition unit of the controller that acquires the first relation information, wherein the circuit of the controller controls the first actuator based on the first relation information acquired by the acquisition unit.

8. The control device according to claim 4 further comprising a memory that stores therein the first relation information.

9. The control device according to claim 4, wherein the bed device further includes a first coupling part, the first coupling part is coupled to the first movable part and the first actuator, and the first coupling part generates the motion of the first movable part in accordance with the motion of the first actuator.

10. The control device according to claim 4, wherein the first actuator extends/contracts or rotates, and the circuit of the controller controls the first actuator based on first state information related to a state of the extension/contraction or the rotation of the first actuator and the first relation information.

11. The control device according to claim 5, wherein the circuit of the controller controls the second actuator based on second relation information related to a relation between a third changing amount of the motion of the second actuator and a fourth changing amount of a motion of the second movable part.

12. The control device according to claim 11, wherein the second actuator extends/contracts or rotates, and the circuit of the controller controls the second actuator based on second state information related to a state of the extension/contraction or the rotation of the second actuator and the second relation information.

13. The control device according to claim 5, wherein the circuit of the controller controls the second actuator such that a second speed of the motion of the second movable part is constant in a period excluding a start motion and an end motion of the second movable part.

14. The control device according to claim 12, wherein the circuit of the controller controls the motion of the first actuator such that a first speed of the motion of the first movable part during a period excluding a motion start and a motion end of the first movable part is constant, and the first speed is identical with the second speed.

15. The control device according to claim 5, wherein the bed device further includes a second coupling part, the second coupling part is coupled to the second movable part and the second actuator, and the second coupling part generates a motion of the second movable part in accordance with a motion of the second actuator.

16. The control device according to claim 4, the first movable part is at a head side of a bed frame, the second movable part is at a foot side of the bed frame, and the first actuator has longer difference between the maximum length and the minimum length than the second actuator.

* * * * *